(12) United States Patent
Azzazy et al.

(10) Patent No.: US 10,537,106 B2
(45) Date of Patent: Jan. 21, 2020

(54) DIRECT DETECTION OF DISEASE BIOMARKERS IN CLINICAL SPECIMENS USING CATIONIC NANOPARTICLE-BASED ASSAYS AND VERSATILE AND GREEN METHODS FOR SYNTHESIS OF ANISOTROPIC SILVER NANOSTRUCTURES

(71) Applicant: AMERICAN UNIVERSITY IN CAIRO (AUC), New Cairo (EG)

(72) Inventors: Hassan Mohamed El-Said Azzazy, Alexandria (EG); Sherif Mohamed Shawky Abduo, Cairo (EG); Kamel Abdelmenem Mohamed Eid, Sharkia Govemorate (EG); Bassem Samy Shenouda Guirgis, Cairo (EG)

(73) Assignee: AMERICAN UNIVERSITY IN CAIRO (AUC), New Cairo (EG)

( * ) Notice: Subject to any disclaimer, the term of this patent is extended or adjusted under 35 U.S.C. 154(b) by 0 days.

(21) Appl. No.: 15/228,759

(22) Filed: Aug. 4, 2016

(65) Prior Publication Data
US 2019/0090491 A1    Mar. 28, 2019

Related U.S. Application Data

(63) Continuation of application No. 14/376,003, filed as application No. PCT/US2013/024136 on Jan. 31, 2013, now abandoned.

(60) Provisional application No. 61/593,019, filed on Jan. 31, 2012, provisional application No. 61/594,817, filed on Feb. 3, 2012.

(51) Int. Cl.
| | | |
|---|---|---|
| *A01N 59/16* | (2006.01) | |
| *G01N 33/552* | (2006.01) | |
| *G01N 33/553* | (2006.01) | |
| *G01N 33/58* | (2006.01) | |
| *C12Q 1/6816* | (2018.01) | |
| *B22F 1/00* | (2006.01) | |
| *B22F 9/20* | (2006.01) | |
| *C12Q 1/70* | (2006.01) | |
| *G01N 33/53* | (2006.01) | |

(52) U.S. Cl.
CPC .......... *A01N 59/16* (2013.01); *B22F 1/0003* (2013.01); *B22F 9/20* (2013.01); *C12Q 1/6816* (2013.01); *C12Q 1/70* (2013.01); *G01N 33/5308* (2013.01); *G01N 33/552* (2013.01); *G01N 33/553* (2013.01); *G01N 33/587* (2013.01); *Y10T 436/143333* (2015.01)

(58) Field of Classification Search
CPC ...... G01N 33/5308; Y10T 436/143333; C12Q 1/6816
See application file for complete search history.

(56) References Cited

U.S. PATENT DOCUMENTS

2011/0054162 A1*  3/2011  Kim .................. B22F 1/0074
                                                   536/25.4

OTHER PUBLICATIONS

Hourfar et al, High-Throughput Purification of Viral RNA Based on Novel Aqueous Chemistry for Nucleic Acid Isolation, 2005, Clinical Chemistry 51, 1217-1222 (Year: 2005).*
Orendorff et al, Aspect ratio dependence on surface enhanced Raman scattering using silver and gold nanorod substrates, 2006, Phys. Chem. Chem. Phys., 165-170. (Year: 2006).*
Sun et al, Atomic force microscopy and surface-enhanced Raman scattering detection of DNA based on DNA-nanoparticle complexes, 2009, Nanotechnology 20, 125502 (12pp) (Year: 2009).*
Summons to attend oral hearing proceedings dated Oct. 10, 2018 issued in corresponding European patent application No. 13742955.1.
Communication dated Feb. 21, 2018 issued in corresponding European patent application No. 13745955.1.
Shawky et al-"Direct detection of unamplified hepatitis C virus RNA using unmodified gold nanoparticles", Clinical Biochemistry 43 (2010) pp. 1163-1168.

* cited by examiner

*Primary Examiner* — Narayan K Bhat
(74) *Attorney, Agent, or Firm* — Oblon, McClelland, Maier & Neustadt, L.L.P.

(57) ABSTRACT

A gold nanoparticle-based assay for the detection of a target molecule, such as Hepatitis C Virus (HCV) RNA in serum samples, that uses positively charged gold nanoparticles (AuNPs) in solution based format. The assay has been tested on 74 serum clinical samples suspected of containing HCV RNA, with 48 and 38 positive and negative samples respectively. The developed assay has a specificity and sensitivity of 96.5% and 92.6% respectively. The results obtained were confirmed by Real-Time PCR, and a concordance of 100% for the negative samples and 89% for the positive samples has been obtained between the Real-Time PCR and the developed AuNPs based assay. Also, a purification method for the HCV RNA has been developed using HCV RNA specific probe conjugated to homemade silica nanoparticles. These silica nanoparticles have been synthesized by modified Stober method. This purification method enhanced the specificity of the developed AuNPs assay. The method can detect a target molecule, such as HCV RNA in serum, by employing modified silica nanoparticles to capture the target from a biological sample followed by detection of the captured target molecule using positively charged AuNPs. The assay is simple, cheap, sensitive and specific. Another aspect of the invention is anisotropic silver nanoparticles and methods of their use.

10 Claims, 16 Drawing Sheets

DIRECT DETECTION OF DISEASE BIOMARKERS IN CLINICAL SPECIMENS USING CATIONIC NANOPARTICLE-BASED ASSAYS AND VERSATILE AND GREEN METHODS FOR SYNTHESIS OF ANISOTROPIC SILVER NANOSTRUCTURES

CROSS-REFERENCE TO RELATED APPLICATIONS

This application is a continuation of U.S. application Ser. No. 14/376,003, filed Jul. 31, 2014, which is a national-stage filing of PCT/US13/024136, filed Jan. 31, 2013, which claims priority under 35 U.S.C. § 119(e) to U.S. Provisional Application 61/593,019, filed Jan. 31, 2012, and to U.S. Provisional Application 61/594,817, filed Feb. 3, 2012, each of the above-mentioned applications are hereby incorporated by reference in its entirety.

BACKGROUND OF THE INVENTION

Field of the Invention

Methods for detecting pathogens using cationic gold- or silver-nanoparticles. The assays can detect amplified and/or unamplified RNA and/or DNA from viruses, bacteria and other organisms, such as Hepatitis C virus and *Mycobacterium tuberculosis*. The invention is also directed to anisotropic silver nanoparticles and methods for synthesizing and using them.

Description of the Related Art

Cationic gold nanoparticle based assays. Many molecular diagnostic assays are commercially available for the detection of several viral/bacterial nucleic acids (DNA/RNA) in patients' blood. Although these assays have high sensitivity and specificity, most of them are time consuming, labor intensive, expensive, and require specialized equipment. Thus for the better control over infectious diseases, especially in developing countries with limited resources including Egypt, the development of novel diagnostic assays that are simple, rapid, sensitive, specific and importantly cost-effective is highly needed. Nanoparticle-based diagnostic assays promise to meet these rigorous demands. Gold and silver nanoparticles (AuNPs, AgNPs) are some of the most promising nanoparticle candidates for diagnosis. They exhibit intense absorbance and scattering properties due to surface Plasmon resonance (SPR). The absorption cross-section of AuNPs was found to be $10^4$ to $10^5$ folds higher than that of the strongest absorbing Rhodamine-6G dye molecule [1]. When AuNPs come close together, plasmon-plasmon coupling occurs leading to energy loss and a shift in the absorbance peak maximum to a longer wavelength and thus a change in color from red to blue occurs [1]. Moreover, AuNP optical properties can be tuned by varying their size and/or shape and AuNPs can be easily synthesized in different size ranges and conjugated to biomolecules such as proteins and oligonucleotides [1].

Developed AuNP-based molecular diagnostic assays can be classified according to the detection signal into colorimetric, scanometric, light-scattering, electrochemical and electrical, quartz-crystal microbalance, Foster Resonance Energy Transfer (FRET) and Nanometal Surface Energy Transfer (NSET), surface enhanced Raman scattering and Laser diffraction assays[1]. Colorimetric detection methods can be further divided into cross-linking (utilizing two oligonucleotide-functionalized AuNP probes), non-cross linking (one probe) and non-functionalized (no probes) using negatively charged AuNPs [1].

Positively charged (cationic) AuNPs have been used in diagnostic assays [2-4]. Sun et al. [5] developed a microarray assay (solid support) for gene expression analysis using cationic AuNPs. First, target molecules are allowed to hybridize with probes immobilized on the solid support and after washing, cationic AuNPs are added. If the target is present, the AuNPs bind to the negatively charged phosphate groups on the DNA target via electrostatic attraction leading to the precipitation of nanogold particles that can easily be detected using a flatbed scanner. Assay sensitivity was estimated to be <2 pg of DNA [5]. Cationic gold nanoparticles also have been used for the determination of DNA chip quality prior to use, Hsiao et al. [6].

A significant drawback to the prior art methods which use gold nanoparticles is that the presence of a capture probe in the absence of a target molecule leads to aggregation of the gold nanoparticles because the capture probes bind to the cationic gold nanoparticles via their phosphate backbones. This increases the percentage of false positive results because the cationic gold nanoparticles aggregated by the capture probe in the absence of the desired target molecule cause a color change from red to blue which is falsely interpreted as detection of the target molecule. Prior art methods require extra steps and labor are required to avoid this problem. Another problem with prior methods is the requirement for equipment that is often not available under field conditions, such as the need to use a scanner to detect hybridization of a target molecule to a capture probe or ligand or the requirement for use of a laboratory spectrophotometer to quantify color change produced by aggregation of gold nanoparticles.

Anisotropic silver nanoparticles. Noble metals such as gold, platinum and silver particles have unique physical, chemical, optoelectronic properties; have been used in catalysis, plasmonics, photography, sensing, drug delivery, imaging, antimicrobial, and information storage and surface enhanced Raman scattering. They also serve as model system for several applications such as electronic or magnetic. Eid & Azzazy, International Journal of Nanomedicine 2012:7 1543-1550 (Mar. 19, 2012) describe hollow flower like silver nanostructures produced by the methods disclosed herein and is incorporated by reference.

Noble metal particles with interior hollow structures play a significant role in drug encapsulation, controlled release of drugs, cosmetics, nucleic acids, removal of pollutants, storage, protection of other chemical reagents and biologically active species. Likewise, the hollow metal particles have been used to modulate refractive index, increase active area for catalysis, improve a particle's ability to withstand cyclic changes in volume, and to expand the array of imaging markers suitable for early detection of cancer.

Properties of nanostructures depend on their size and shape which subsequently determine their possible utilizations for instance SERS, antimicrobial, catalytic effect have been depended on the morphology of silver particles.

Current chemical, physical, biological methods for synthesis of anisotropic nanostructures include the silver mirror reaction, polyol process, seed-mediated, light-mediated, and template-directed growth, and lithographic fabrication.

Hollow nanoparticle structures can be fabricated by several methods such as conventional hard templates, sacrificial templates, soft templates, template-free methods. Similarly, hollow metallic nanostructures have been fabricated by electrodeposition of thin layer of another metal or salts followed by calcinations or etching.

The difficulties encountered in fabricating anisotropic, controlled hollow nanostructures include high cost, the use of toxic chemicals, and expensive and complex laboratory equipment requiring highly skilled technicians. Thus, there is a need for methods of fabricating these structures that are faster, less complicated and less expensive. Moreover, there is a need to develop new kinds of nanostructures with different geometries that provide useful functionalities, for example, for diagnostic or therapeutic use or for studying plasmonic and other functional properties of metallic nanoparticles.

One of the unique, promising tools in various application the hollow metallic structures due to their lower density, higher surface, enhancing their antimicrobial effects and other related properties. Physical characteristics of hollow metallic nanostructures that contribute to their useful diagnostic and therapeutic properties include their low density compared to solid nanoparticles, a relatively high surface area to mass, and their capacity to be loaded or coated with other agents used for diagnosis or therapy.

Similarly, the development of nanoparticles with unique geometric shapes permits control of their physical properties, including size, density, surface area to mass, and loading capacity. Control of size and geometry is relevant to the bioavailability of the nanoparticle per se or to covalent- or non-covalent complex of the nanoparticle with other active components, such as diagnostic or therapeutic agents. For example, size and geometry affect the biological absorption, uptake, targeting, and/or persistence of such nanoparticles.

As apparent from the background references, there is a need for new methods that are environmentally sound (green), fast and inexpensive. Such methods would not require the use of undesirable polymers, surfactants or non-biodegradable reagents or require the use of complex laboratory equipment, but would permit synthesis of nanoparticles in a very short time while permitting control over their size and geometry and parameters like density and surface area. Ideally, such a method would provide a variety of different kinds, sizes and geometries of nanostructures.

BRIEF SUMMARY OF THE INVENTION

Gold nanoparticle based assays. The present invention solves problems associated with the use of gold nanoparticles for detection of target molecules. It detects unknown target molecules, such as RNA or DNA in a biological sample in a homogenous based solution, thus avoiding the requirement of having to hybridize a nucleic acid in a sample (or attach other target molecules like polypeptides) to a probe (or ligand) on a solid support. This avoids the problem of false positives caused by aggregation of a capture probe with the cationic gold nanoparticles because the gold nanoparticles are not brought into contact with capture probes.

One way the invention accomplishes this is through the use of silica or magnetic nanoparticles which are attached to a specific probe (e.g., a capture probe for HCV RNA) or specific capture ligand (e.g., for a specific polypeptide or other molecule). This mode of capture differs significantly from prior art methods that use gold nanoparticles to confirm the capture of a target molecule. The invention uses the silica or magnetic nanoparticles that are specifically attached to a specific capture probe (or ligand) by a crosslinker to isolate or purify the target molecule from a solution containing many molecules, such as a complex mixture containing HCV RNA and many other nucleic acids. The invention thus avoids the problem of false positives caused by aggregation of gold nanoparticles when the target molecule is absent from a sample. For example, cationic gold nanoparticles can aggregate non-specifically in the presence of contaminating non-target nucleic acids due to interaction of the phosphate backbone of contaminating nucleic acids (i.e., non-target nucleic acids) or capture probes, thus producing a false positive reading. The invention avoids such false positive readings by separating the step of capturing a target nucleic acid from its detection by cationic gold nanoparticles. For example, the cationic gold nanoparticles do not come into contact with a capture probe for HCV RNA or the contaminating nucleic acids in a sample from a subject suspected of being infected by HCV. This eliminates or substantially reduces false positives due to aggregation of cationic gold nanoparticles with a capture probe or a contaminating nucleic acid in a biological sample.

Advantageously the invention provides a homogenous based assay, which specifically detects target molecules, such as HCV RNA, that is simple and can be used outside of a hospital or medical laboratory (e.g., in the field) to detect the target molecule visually by the naked eye without equipment like a scanner. The invention also provides a method of determining the amount of the target molecule in a sample because the color change produced by the aggregation of cationic gold nanoparticles in the presence of a target molecule is directly proportional to the target concentration in a biological sample. Quantification does not require the use of equipment often unavailable in the field, such as the use of a spectrophotometer. It may be performed simply by comparing the degree of color change produced by aggregation of the cationic gold nanoparticles based on comparison with a standard of known concentrations of target molecules. Alternatively, the method according to the invention may be performed by measuring color intensity using a portable spectrophotometer. In one aspect, the invention is directed to a method for detecting a material or molecule of interest, such as a nucleic acid, peptide, polypeptide or a protein, comprising: contacting a sample suspected of containing the material or molecule of interest, such as a nucleic acid or a protein to be detected, with positively charged gold and/or silver nanoparticles; determining the aggregation of nanoparticles after contacting them with the sample; and detecting the nucleic acid or the protein in the sample when the nanoparticles aggregate in comparison with a control sample that does not contain the nucleic acid or the protein to be detected.

This method may be used to detect nucleic acids, modified nucleic acids, or aptamers of nucleic acids, including DNA and RNA molecules. Examples of nucleic acids to be detected by this method include those selected from the group consisting of single stranded RNA, single stranded DNA, double stranded DNA, stem loop RNA, positive strand RNA, negative strand RNA, and double stranded RNA. These nucleic acids may be viral nucleic acids, such as RNA from HCV (hepatitis C virus) or nucleic acids amplified from viral sources. The invention also contemplates detection of nucleic acids from or amplified from non-viral sources, including detection of nucleic acids or other kinds of molecules from bacteria, mycobacteria, yeast, fungi, parasites, or other kinds of pathogens, as well as nucleic acids from other sources, such as from eukaryotic organisms including non-human animals or from humans.

This method is not limited to detecting only nucleic acids, but can be used to detect other kinds of molecules, such as for detecting a peptide, polypeptide or protein. For example, it can be used to detect a protein that is an enzyme, antigen, antibody, a folded protein, an unfolded protein, a reduced protein, a non-reduced protein, or a tumor marker.

The method may be applied using samples obtained from various sources, such as from blood, plasma, serum, serum, optionally containing EDTA, spinal fluid, saliva, urine, mucosal secretions and other biological fluids or tissues. Samples may be obtained from normal subjects, for example, for routine screening or testing, or from subjects at risk for, suspected of having, or who have been diagnosed with a particular condition, disorder or disease. Examples of such subjects include patients having a viral disease, undergoing treatment for a viral disease, or suspected of having a viral disease; patients having a bacterial disease, undergoing treatment for a bacterial or mycobacterial disease, or suspected of having a bacterial disease and patients having a fungal or parasitic disease, undergoing treatment for a fungal or parasitic disease, or suspected of having a fungal or parasitic disease. Samples may be obtained from subjects at different times or stages of a condition, disorder or disease, such as during an acute, chronic or occult phase. Samples may be obtained longitudinally from a patient during the course of a disease or during or after treatment, for example, at least 1, 2, 4, 8, 12, 16, 20, 24, 28, 32, 36, 40, 44, 48, or 52 weeks during or after cessation of therapy for a microbial disease, disorder or condition.

This detection method may be practiced using positively charged gold nanoparticles or positively charged silver nanoparticles. These nanoparticles preferably are spherical or spheroidal in geometry and have average diameters of 12 to 40 nm, for example 15-18 nm or any intermediate sub-range or value within these ranges, including 12, 13, 14, 15, 16, 17, 18, 19, 20, 21, 22, 23, 24, 25, 30, 35 and 40 nm. Nanoparticles that are not spherical may also be employed, such as rod-shaped particles (nanorods) having any aspect ratio, star-shaped nanoparticles, or particles having other unique geometries.

In a detection method, the aggregation of the gold nanoparticles, which indicates detection of a positive sample, can be detected by a blue color and non-aggregated gold nanoparticles by a red color. A positive sample can be detected using silver nanoparticles based on color change from yellow to colorless or to a white precipitate.

Prior to detection, a sample may be processed, for example, extracted, isolated, purified or concentrated prior to contacting it with the gold and/or silver nanoparticles. One predetection processing method contacts a sample with silica nanoparticles conjugated to a ligand that binds to a molecular target, such as a specific polynucleotide or polypeptide, to be detected (or that binds to a substance, composition, solution, or aggregate containing the target molecule. The target molecule binds to or is adsorbed to the silica nanoparticles, can be washed or separated from other components in a sample, and then eluted, separated or otherwise recovered from the silica nanoparticles in a less complex mixture or in a more concentrated or purified form.

In another embodiment, the invention is directed to a method for capturing at least one biological material of interest comprising contacting the material to be captured with silica nanoparticles or another kind of suitable nanoparticle for a time and under conditions sufficient for the material to bind to the silica nanoparticles and then optionally eluting the captured material from the silica nanoparticles and/or further purification or characterization of the captured and released material.

This method may be used to capture a biological material that is a nucleic acid, a synthetic or modified nucleic acid, a peptide, polypeptide, protein or protein complex (e.g., protein dimers or trimers or aggregates in which a protein is associated with other molecules) or other biological components of interest. The material of interest may be obtained from a virus, bacterium, *mycobacterium*, yeast, fungus, parasite or other microorganism as well as from other kinds of cells including mammalian or human cells or samples, or from extracts or components from these sources.

This capture method may also employ silica nanoparticles conjugated to a ligand for the target molecule, such as a polynucleotide sequence that is complementary to a target polynucleotide or that is an aptamer that binds to the nucleic acid to be detected. For example, the silica nanoparticles can be conjugated to a ligand that binds to material containing or associated with the nucleic acid to be detected and the method can further involve isolating or purifying the nucleic acid from the material bound to the silica nanoparticles. Similarly, other materials, including polypeptides, glycopolypeptides, lipids and carbohydrates can be captured using molecules that bind to them which have been bound to or associated with silica nanoparticles.

Those of skill in the art may select various ligands for use in this capture method. Examples of such ligands include antibodies or fragments of antibodies containing binding sites such as those of IgA, IgD, IgE, IgG, IgM and the various subtypes of these kinds of antibodies.

This capture method may be employ a ligand that is an aptamer that binds to a protein, carbohydrate, lipid or other material associated with the nucleic acid to be captured or detected. It also may employ ligands, such as DNA or RNA or a complex or aggregate of a nucleic acid with a peptide, polypeptide or protein, that bind directly to a target molecule or target material to be captured or detected.

The ligand in this capture method may comprise various lectins, such as one or more mannose binding lectin(s), one or more N-acetyl glucosamine(s) with or without sialic acid binding lectin(s); one or more galactose/N-acetylgalactosamine binding lectin(s); one or more N-acetylneuraminic acid binding lectin(s); or one or more fucose binding lectin(s).

The ligand used in this method may be a specific probe for the nucleic acid to be detected that is conjugated to at least one member selected from the group consisting of iron oxide, gold, silver, quantum dots and silica nanoparticles of different sizes.

The method may further involve extracting the nucleic acid from the material containing it or from the material from which it is associated which has been bound to said ligand. It also may comprise contacting the sample with nanoparticles selected from the group consisting of iron oxide, gold, silver, quantum dots and silica nanoparticles, which have been conjugated to a probe comprising an oligotargeter sequence. For example, the sample may be contacted with at least one oligotargeter selected from the group consisting of SEQ ID NO: 1, 2, 3, 4, or 5.

Another specific aspect of the invention is a method for detecting HCV RNA in a sample comprising one or more of the following steps: processing a sample suspected of containing HCV RNA to obtain a sample containing HCV RNA, contacting the isolated RNA with silica nanoparticles conjugated to a nucleic acid or aptamer complementary to HCV RNA, removing material that is not bound to the silica nanoparticles, eluting RNA bound to the silica nanoparticles, contacting the eluted RNA with cationic gold and/or silver nanoparticles, and detecting HCV RNA when the cationic gold aggregate, wherein aggregation may be determined calorimetrically by a color change from red (substantially not aggregated nanoparticles) to blue (aggregated nanoparticles) for the gold nanoparticles, or wherein aggregation of cationic silver nanoparticles may be determined calorimetrically by color change from yellow (substantially non aggregated nanoparticles) to colorless or to white precipitate (aggregated nanoparticles).

A specific embodiment of the invention is a method for the capture of one or more target molecules (e.g., a specific nucleic acid or protein biomarker) using modified silica nanoparticles. Once captured and recovered, the biomarkers or target molecules are detecting using unmodified cationic gold nanoparticles or cationic silver nanoparticles. Once a biomarker is captured and contacted with the cationic gold or silver nanoparticles, it can be detected colorimetrically (e.g., visually) or spectrophotometrically.

The methods described herein can be applied to real clinical specimens in either a solution assay format or in a solid support assay format. The solution assay format starts by adding the target to a mixture of cationic nanoparticles and phosphate buffer, in case of positive sample the color changes within 2 minutes into blue color while remains red in the negative samples. On the other hand, the solid format assay starts by first immobilizing the captured probes on the solid support, then the target is added onto the plate and allowed to hybridize with the immobilized probes and then washing with phosphate buffer to remove excess reagents and targets, finally, the cationic nanoparticles are added, in case of positive samples the color changes from red to blue while, remains red in case of negative sample.

Another embodiment of the invention is kit comprising positively charged gold and/or silver nanoparticles; a ligand, such as an antibody, aptamer, lectin, or probe, which is conjugated to iron oxide, gold, silver, quantum dots or silica nanoparticles (or other suitable nanoparticles), and optionally, at least one biological sample preservative, buffer or additive, a nucleic acid extractant buffer, a reaction buffer, a negative control sample, a positive control sample, a reaction container, a colorimetric chart, a packaging material, guide, and/or an instruction for use in detecting or capturing a nucleic acid or other biological molecule.

Anisotropic silver nanoparticles: The inventors have discovered and developed methods having these unique advantages compared to the background art for silver nanoparticles. The methods are:

green, fast, and inexpensive;

do not require polymers, surfactants, or toxic, nondegradable reagents; and are uncomplicated to perform and do not require sophisticated laboratory equipment or extensively trained technicians.

These methods synthesize nanoparticles, such as hollow silver nanoparticles with a variety of geometries and sizes in a very short time, for example, in less than 10 min. These methods allow control over the size, morphology, density and surface area of nanoparticles and the pores or hollow spaces in silver nanoparticles and synthesize a wide variety of anisotropic silver nanostructures, including unique 3d floral (flowerlike) nanostructures. Some nonlimited embodiments of the invention are described below.

A method for synthesizing silver nanoparticles comprising chemically reducing a precursor silver compound in the presence of a reducing agent and a capping agent for a time and under conditions sufficient to produce silver nanoparticles. Examples of the silver precursor compound include silver nitrate, silver acetate, silver chloride, or other kinds of silver salts and examples of a reducing agent include both ascorbic acid and dextrose, or combinations of reducing agents. Some examples of a capping agent are citric acid, sodium citrate, potassium citrate, or other kinds of citrate salts.

Specific embodiments of this method include reducing the precursor silver compound with ascorbic acid, with ascorbic acid and NaOH, with dextrose, with dextrose and NaOH, with ascorbic acid and dextrose, or with ascorbic acid and dextrose and NaOH. In other specific embodiments of this method the capping agent will be trisodium citrate, or the capping agent and/or morphology controlling agent will be only dextrose, only dextrose and citrate. A capping and/or morphology controlling agent may also constitute one of the above-mentioned agents, like citrate, in combination with one or more polymers, for example, citrate in combination with at least one polymer selected from the group consisting of PEG, PVA, PMMA, PEI, CMC and chitosan.

In conjunction with this method the precursor silver compound, reducing agent and capping and/or morphology controlling agent may be dissolved in water or in another aqueous solution. In an alternative embodiment, the precursor silver compound, reducing agent and capping agent are dissolved in an organic solvent or in a mixture of water and an organic solvent.

One of skill in the art may select appropriate physical conditions, such as temperature and pressure for performing this method. For example, the method may be conducted at a temperature below room temperature, at room temperature, or at temperature above room temperature or by gently heating the precursor silver compound and reducing agent. The method can performed at standard atmospheric pressure or at a pressure above or below standard atmospheric pressure.

The morphology of the silver nanoparticle produced by this method can be controlled by selecting particular concentrations or ratios of the silver precursor compound(s), reducing agent(s), and/or capping agent(s), including polymer concentration if present. Variable concentrations of these ingredients or physical conditions may be provided during the reaction producing the silver nanoparticles. The size and morphology of the nanoparticles can be controlled by adjusting the pH, temperature, pressure and/or UV or other kinds of radiation as well as by the other conditions described above. For example, the size of the nanostructures produced can be reduced by using a lower concentration of silver compound or reducing agent than that used in an otherwise identical method that produces larger nanostructures or vice versa. The size of the nanostructures may also be reduced by using a lower concentration of silver compound or reducing agent and a higher intensity of, higher wavelength of, or longer exposure time to, UV or other kinds of irradiation than that used in an otherwise identical method that produces larger nanostructures and vice versa. The terms nanoparticles and microparticles comprise those having particle sizes in the ranges of 1-1,000 nm and 1,000-10,000 nm; respectively.

Other specific embodiments of this method include one that uses ascorbic acid as a reducing agent, citrate as a capping and/or shape control agent and which takes place at room temperature; one that uses ascorbic acid as a reducing agent, citrate and one or more polymer(s) as a capping and/or shape control agents and which takes place in the absence of UV irradiation; one that uses ascorbic acid as a reducing agent, citrate as a capping and/or shape control agent and which takes place in the presence of UV irradiation.

Another embodiment of the invention is a method for synthesizing gold, platinum or palladium (or other noble metal) nanoparticles comprising chemically reducing a precursor gold, platinum, palladium or other noble metal compound in the presence of a reducing agent and a capping agent for a time and under conditions sufficient to produce gold, platinum or palladium nanoparticles or microparticles.

These methods produce different kinds of nanoparticles or microparticles which are described in more detail below and by the figures. These include nanoparticles or microparticles exhibiting a dendritic or fractal pattern; methods that produce a solid, lattice-like, hollow, layered and/or generally symmetrical nanoparticle or microparticle; methods that produce a nanoparticle or microparticle that does not exhibit a dendritic or fractal pattern; or methods that produce a nanoparticle or microparticle that is not solid, lattice-like, hollow, layered and/or generally symmetrical.

The invention is also directed to embodiments represented or characterized by particular kinds of nanostructures. These include, but are not limited to a nanostructure or microstructure produced by or producible by the any of the methods or various combinations of conditions described above. Such nanostructures include a floral or flower-like nanostructure or microstructure; a cube or cuboid nanostructure or microstructure; a dendrimer nanostructure or microstructure; a bipod nanostructure or microstructure; a myriad dendrimer nanostructure or microstructure, which has soft or smooth arms; a star-shaped nanostructure or microstructure that has soft or smooth arms; a star-shaped nanostructure or microstructure that has rough arms; a star-shaped nanostructure or microstructure having soft or rough arms containing hole(s) or an empty core; a floral or flower-like nanostructure or microstructure having soft or smooth arms; a floral or flower-like nanostructure or microstructure having soft or smooth arms with a hole(s) or an empty core; a myriad dendrimers nanostructure or microstructure having soft or smooth arms; a butterfly-like nanostructure or microstructure having soft or smooth branched wing-like arms; a star-like nanostructure or microstructure having soft or smooth arms with multiple layers of arms; a star-like nanostructure or microstructure having rough arms and multiple layers of arms; a star-like nanostructure or microstructure having soft or smooth branched arms and multiple layers of arms; a star-like nanostructure or microstructure having rough, branched arms and multiple layers of arms; a floral or flower-like nanostructure or microstructure having soft arms and multiple layers of arms; a floral or flower-like nanostructure or microstructure having rough arms and multiple layers of arms; a butterfly-like nanostructure or microstructure having soft or smooth wing-like arms and multiple layers of arms; a butterfly-like nanostructure or microstructure having rough, branched wing-like arms and multiple layers of arms; a 3d floral or flower-like nanostructure or microstructure having multiple layers of hollows, rough surface, and external channels surrounding the nanostructure particles substantially as shown in FIG. 1; a 3d floral or flower-like nanostructure or microstructure having multiple layered hollow rough surfaces, large holes, highly external channels surround the nanostructure substantially as shown by FIG. 2; a 3d shell-like silver nanostructure or microstructure with little hollow pores, rough surface, highly external arms substantially as shown by FIG. 3; a 3d scaffold-like silver nanostructure or microstructure with little hollow pores, and a rough surface substantially as shown by FIG. 4; a 3d roll fiber twin-like silver structures with little hollow pores, rough surface, highly external arms substantially as shown by FIG. 5; porous spherical-like silver nanostructures with little hollow pores and rough surface substantially as shown by FIG. 6; porous spherical sponge-like silver nanostructures with high inter-connected pores and rough surface substantially as shown by FIG. 7; 3d flower-like silver nanostructures with multi external interacted layers of hollow, branched rough edges substantially as shown by FIG. 8; a flower-like silver nanostructures with multi layers of paper, hollow cores, soft surface substantially as shown by FIG. 9; a tree-like silver nanostructures with multi-branched edges/arms substantially as shown by FIG. 10; a flower-like silver nanostructure with more wide internal hollow core, multi-edges/arms; dendrimer silver nanostructures with highly branched arms; flower silver nanostructures with more internal hollow pores and rough surface; octahedral multi layer silver nanostructures; octahedral multi-layered nanostructures with pores on the surface; ribbed silver nanostructures; multi-ribbed nanostructures with cubes decorated on the surface of the silver structures; octahedral structures with cubes decorated on the surface silver structures; silver stars with soft, rough arms produced by a method described herein that allows control of their size and morphology; silver flowers with soft arms, produced by a method described above allowing control of their size and morphology; myriad dendrimer with branched arms substantially produced by a method that permit the control of their size and morphology; silver butterfly-like structures with arms/wings substantially produced by a method that allows control of their size and morphology. These nanoparticles or microparticles can be produced by the methods described herein as well as by equivalent methods that make the same kinds of structures.

Other embodiments represent compositions containing or comprising nanoparticles or microparticles according to the invention, such as those containing one or more additional ingredients, such as one or more pharmaceutically or diagnostically suitable ingredients, which may be covalently or non-covalently associated with the nanostructure, or microstructure. A size selected or refined nanoparticle or microparticle composition may also be produced by selectively removing nanostructures or microstructures, based on their size or morphology, for example, as produced by filtration, centrifugation, or sedimentation to recover nanostructures having a particular morphology and/or size.

Other inventive embodiments include methods of using the nano- or microstructures described herein. These include a method for antimicrobial therapy comprising contacting a microbe or a host cell a nano- or microparticle as described herein. A method of diagnosis comprising processing or contacting a biological sample with a nano- or microparticle as described herein. A method for detecting a molecule or substance comprising contacting a sample with a nano- or microparticle as described herein under conditions suitable for SERS. A method for optically detecting a molecule or substance comprising contacting a sample with a nano- or microparticle as described herein under conditions suitable for optical detection. A method for optically detecting a molecule or substance comprising contacting a sample with a nano- or microparticle as described herein under conditions suitable for optoelectronic detection or operation. A method for biosensing comprising incorporating a nano- or microparticle as described herein into a device or a biosensor. A method for tissue engineering, treatment or modification comprising contacting a tissue with a nano- or microparticle as described herein. An imaging method comprising contact a sample to be imaged with a nano- or microparticle as described herein. A method for modeling a system, such as a biological system, comprising contacting a system with a nano- or microparticle as described herein. A waveguide or electronic device comprising a nano- or microparticle as described herein. An ink, stain, dye, pigment, primer, paint or anticorrosive agent comprising a nanoparticle made by the methods describe herein. A resin, plastic, rubber, putty, or glass comprising nanoparticles made by the methods described herein. An agent added to a product or composition to identify, tag it, track it or to otherwise identify it or its properties comprising nanoparticles made by the methods describe herein. A composite that enhances thermal, electrical or magnetic conduction comprising nanoparticles made by the methods described herein. A composition that attenuates thermal, electrical or magnetic conduction comprising nanoparticles made by a method according to the invention. A bleach, surfactant, laundry detergent, soap, antimicrobial agent, antiseptic, or cleaning agent comprising nanoparticles made by a method according to the invention. A filter, HEPA filter, face mask, catalyst, or detoxifying agent or substrate comprising a nanoparticles made by a method according to the invention. A medical device, medical equipment or medical supplies, such as bandages, wound dressings or biological implant such as a heart valve, comprising nanoparticles made by a method according to the invention. A dental device, prosthetic, dental equipment or dental supply, such as a dental metal alloy or artificial tooth or implant, comprising nanoparticles made by a method according to the invention. A cosmetic or dermatological product comprising nanoparticles made by a method of according to the invention. A microelectromechanical system (MEMS) comprising nanoparticles made by a method according to the invention. An explosive, primer, propellant, shell, ammunition, weapon, or other ordnance comprising nanoparticles made by the methods described herein. A consumer product, such as a toy, food storage container, baby pacifier, clothing, jewelry, metal, plastic or glass decoration comprising nanoparticles made by the methods described herein. A method for evaluating the safety of nanoparticles made by the methods according to the invention comprising contacting a cell or an organism with said nanoparticles, measuring at least one biological effect of said nanoparticles on the cell or organism in comparison with an otherwise identical cell or organism not exposed to said nanoparticles.

BRIEF DESCRIPTION OF THE DRAWINGS

FIG. 3.

FIG. 5.

FIG. 6.

PART 1: DETAILED DESCRIPTION OF THE INVENTION

Gold Nanoparticle-Based Assays.

The inventors have developed for the first time an AuNP-based colorimetric method (solution phase) utilizing non-functionalized positively charged AuNPs for the direct detection of unamplified RNA and/or DNA molecules extracted from clinical specimens. This method can be applied to identify biomarkers of diseases such as nucleic acids and/or proteins from eukaryotic or prokaryotic sources particularly that of pathogens. In the examples shown below, Hepatitis C Virus (HCV) RNA was used as a model for testing the efficiency and specificity of the developed assay, which was used for the direct and specific detection of unamplified HCV RNA extracted from clinical samples.

Figure 1:
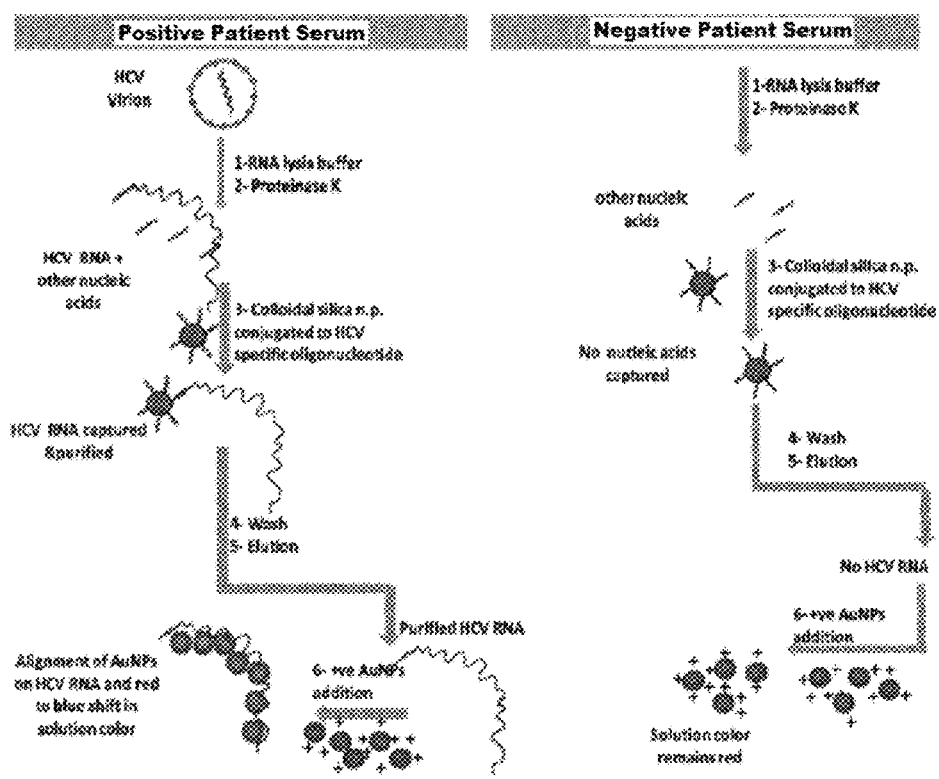
FIG. 1. Flow chart of one embodiment of a cationic AuNP-based assay. HCV virions are first lysed with RNA lysis buffer and proteins are digested by Proteinase K. HCV RNA present in the digested lysate is captured with silica nanoparticles conjugated to an oligonucleotide specific for the target HCV RNA. The captured target RNA is then washed and then eluted in a purified form. The purified RNA is added to AuNPs in a phosphate buffer. A color change from red to blue observed within about 2 minutes. This change in color occurs due to alignment of the positively charged AuNPs on the phosphate backbone of the HCV RNA. AuNPs in samples to which no RNA is added do not aggregate and remain red.

HCV is a major global health problem as it infects about 200 million individuals worldwide, with 3-4 million newly infected annually [7]. Chronic Hepatitis C develops in about 70-90% of cases and about 5-20% and 1-5% of chronically infected patients develop cirrhosis and hepatocellular carcinoma (HCC), respectively [8]. As illustrated in FIG. 1, this method can employ a selective extraction method that captures the nucleic acid of interest from clinical specimens and then colorimetrically identify the captured nucleic acid. This method is simple, rapid, highly sensitive, specific and cost-effective.

Figure 4:
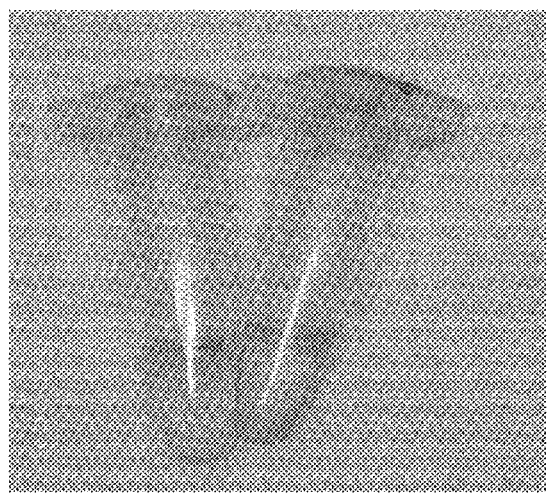
FIG. 4. Analysis of clinical specimens using AuNP-based assay. In the absence of HCV RNA, the AuNPs are positively charged and are separated from each other by repulsion and the solution is red in color. On the other hand, in samples containing HCV RNA the AuNPs align on the phosphate backbone of the HCV RNA changing the color of these HCV RNA-positive samples from red to blue.

HCV RNA was extracted using a commercially available viral RNA extraction kit (Promega). Extracted HCV RNA was then added to the positively-charged AuNPs. In case of positive samples, the positively-charged AuNPs bind to the negatively-charged phosphate groups on the HCV RNA target via electrostatic attraction between the negatively charged RNA phosphate backbone and the positively charged CTAB capping on AuNPs leading to Plasmon-Plasmon interaction and a change in the solution colour from red to blue [2, 13]. In the absence of HCV RNA (absence of any nucleic acid), the AuNPs are far from each other (repulsion between positively-charged particles) and thus the solution colour remains red (FIG. 4). Since the developed assay utilizes positively-charged AuNPs instead of negatively charged ones for HCV RNA detection, the test is more direct and simpler requiring minimal optimization. It is important to note that the red colour is stable even when left undisturbed for several days. Thus, the developed assay can simply and rapidly (about 5 min) determine any nucleic acid (RNA and/or DNA single or double stranded) in the solution. The reported sensitivity and specificity is 91%. and 94.8%, respectively.

Figure 7:
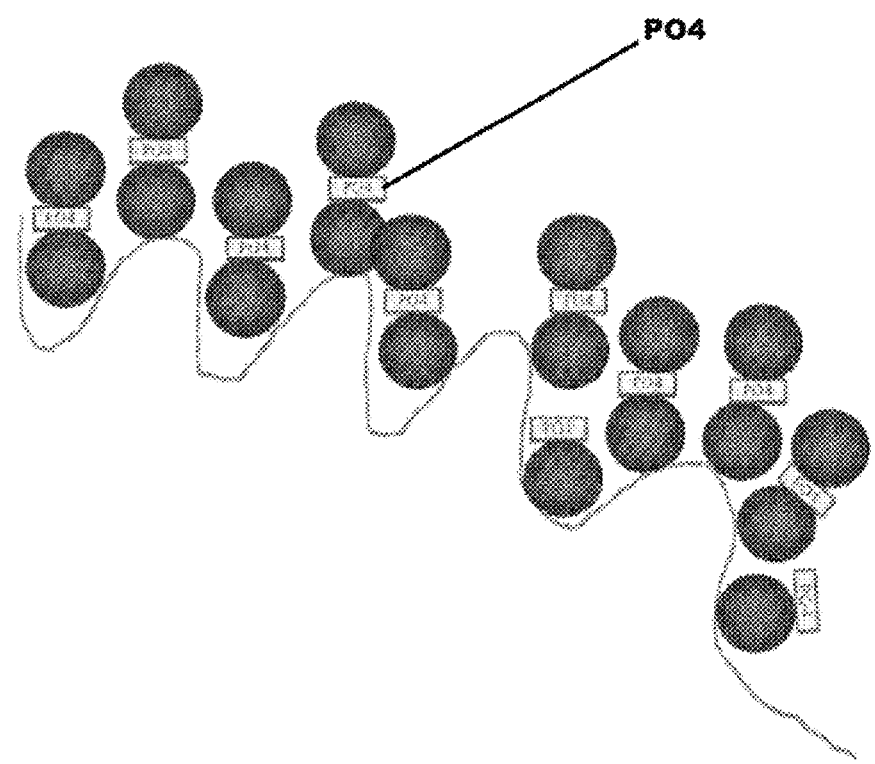
FIG. 7 illustrates the mechanism of how cationic AuNPs aggregate along a strand of nucleic acid.

The presence of nucleic acid in the sample, leads to alignment of the positively charged AuNPs on the phosphate backbone of the nucleic acid, the presence of phosphate buffer in the assay increases the aggregation capability of the AuNPs (for only the positive samples) by binding of the phosphate ions to the aligned AuNPs and then another row of AuNPs attached to the other part of the phosphate ions which will be aligned on another phosphate backbone of another RNA molecule (FIG. 7). So, aggregation occurs by first alignment of AuNPs on phosphate backbone of one nucleic acid, which then binds to phosphate ions and the latter binds to another AuNPs which are aligned on another nucleic acid phosphate backbone. Therefore, at least 5 layers are formed in the positive samples and leads to AuNPs aggregation, the layers are: 1stRNA/AuNPs/Phosphate ions/AuNPs/2ndRNA. These layers will result in forming a network of nucleic acid/AuNPs which lead to aggregation of gold nanoparticles and change of colour from red to blue.

To increase specificity and sensitivity of the assay, HCV RNA specific probe conjugated to silica and/or magnetic nanoparticles have been used for viral RNA capture after lysis the virion and precipitation of the proteins in the sample so a simple, rapid, specific and direct magnetic/silica-probe based extraction method has been developed and when coupled with the AuNP based colorimetric assay a sensitivity and specificity of 92.6% and 96.5%, respectively, was obtained.

The invention is not limited to a particular method for synthesizing cationic (positively charged) gold nanoparticles (AuNPs) or silver nanoparticles (AgNPs). Various methods may be used. General synthesis methods for producing positively charged gold nanoparticles are based mainly on the reduction of hydrogen tetrachloroaurate trihydrate ($HAuCl_4$) using sodium borohydride as a reducing agent, in the presence of the capping agent. Changing concentration of the different reagents, reaction time and pH will determine the final size and shape of the prepared nanoparticles. The common used capping agents are:

(i) cetyl trimethyl ammonium bromide (CTAB), see Narayanan R, Lipert R. J, Porter M D. Cetyltrimethylammonium bromide-modified spherical and cube-like gold nanoparticles as extrinsic Raman labels in surface-enhanced Raman spectroscopy based heterogeneous immunoassays. Analytical chemistry. 2008, 80(6): 2265-71; and Wenlong Cheng, Shaojun Dong, Erkang Wang. Synthesis and self assembly of cetyltrimethylammonium bromide capped gold nanoparticles. Langmuir. 2003, 19(22): 9434-39 (both of which are incorporated by reference);

(ii) cysteamine, see Kim J W, Kim J H, Chung S J, Chung B H. An operationally simple colorimetric assay of hyaluronidase activity using cationic gold nanoparticles. Analyst. 2009 July; 134(7):1291-3; or T. Niidome et al. Preparation of primary amine-modified gold nanoparticles and their transfection ability into cultivated cells. Chem. Commun. 2004, (17):1978-1979 (both of which are incorporated by reference); and (iii) lysine, see P R. Selvakannan et al. Capping of gold nanoparticles by the amino acid lysine renders them water dispersible. Langmuir. 2003, 19(8): 3345-49 (which is incorporated by reference).

Methods used for synthesis of positively charged silver nanoparticles (AgNPs), are similar to those used for the gold nanoparticles [9], and based on the reduction of silver salt in the presence of capping agents as CTAB [10, 11], polyethylimine (PEI) [12] and p-benzoquinone [13]. Silver nanoparticles based assays are based on change of color of the silver nanoparticles solution from yellow to colorless and/or formation of white precipitate based on the degree of aggregation.

The present invention is described below based on some specific examples which pertain to some specific embodiments of the invention. However, the invention is not limited to what is described in these examples.

EXAMPLES

Example 1: Detection of HCV RNA in Serum Samples

Synthesis of Positively-Charged AuNPs.

Positively charged spherical particles were synthesized as previously described in [14]. Briefly, the seed solution was prepared by reducing $HAuCl_4$ (2.5 ml of 0.001 M $HAuCl_4$), in presence of CTAB (7.5 ml of 0.2 M), with ice-cold $NaBH_4$ (600 µL; 0.01 M). The vials were then shaken vigorously (about 2 min) to produce brown seed suspensions. The seed (80 µl) was then added to the centre of a solution containing $HAuCl_4$ (50 ml of 0.001 M $HAuCl_4$), CTAB/BDAC mixture (50 mL containing 0.2 M of CTAB plus 0.25M of BDAC), $AgNO_3$ (1.5 mL of 0.004 M $AgNO_3$) and ascorbic acid (700 µl of 0.0788 M). The mixture was left undisturbed for about 24 h.

Characterization of Synthesized AuNPs.

Figure 2:
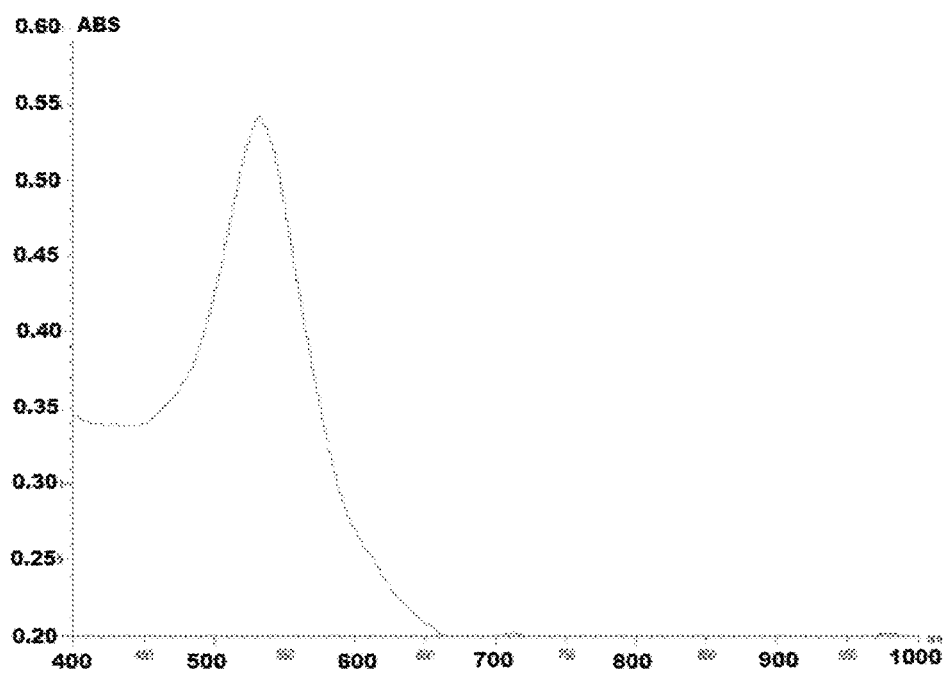
FIG. 2. UV-Vis spectrum of the positive AuNPs. The spectrum shows a $\lambda_{max}$ at 531 nm characteristic of spherical AuNPs.
Figure 3A:
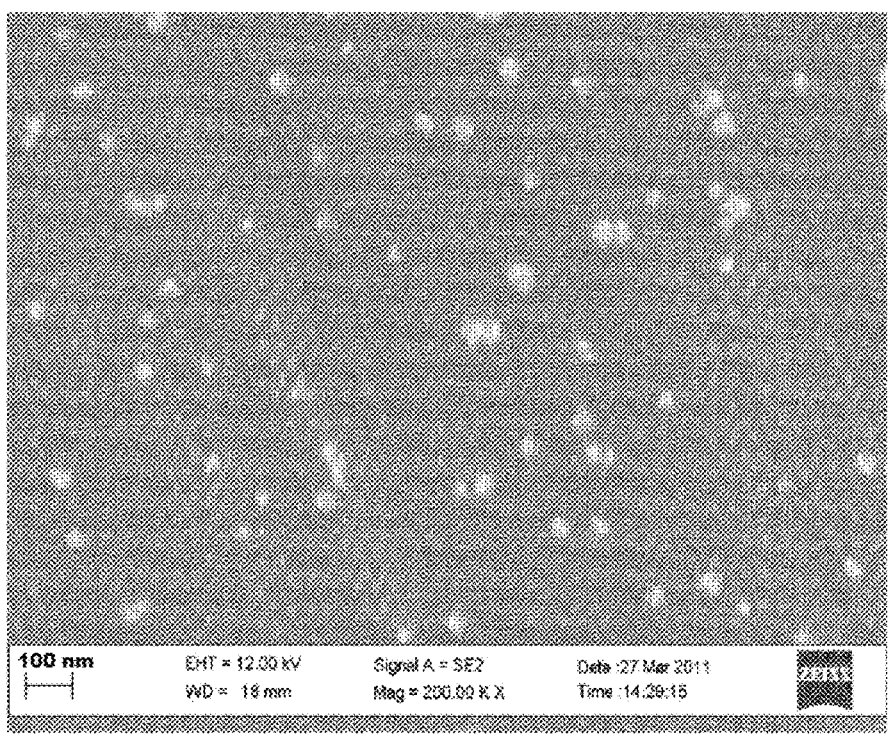
(FIG. 3A) SEM of the prepared AuNPs.
Figure 3B:
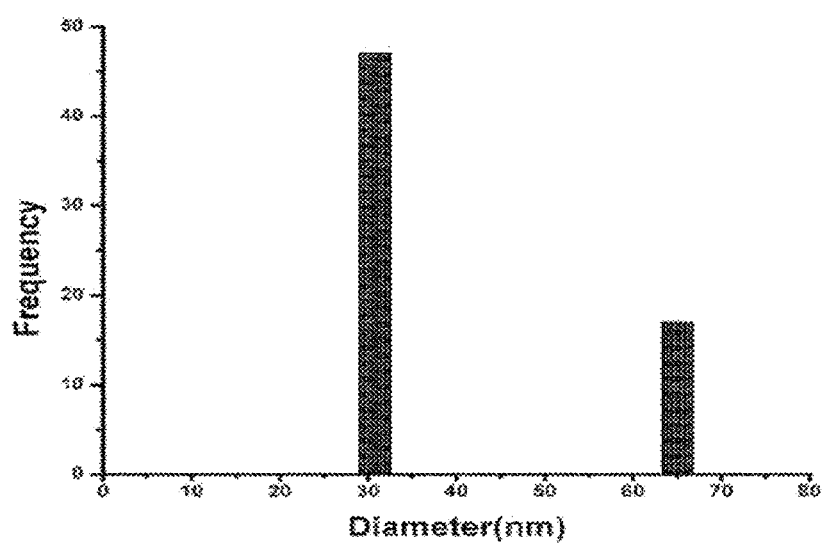
(FIG. 3B) The particles have an average diameter of about 30 nm.

The absorbance spectrum and concentration of the positively charged particles were determined using UV spectrophotometer (Jenway 6800) as previously reported in [15]. The shape and size of the produced positively charged particles were analyzed using field emission scanning electron microscopy (SEM; Model: Leo Supra 55; US). For the SEM analysis, 5 µl of the synthesized AuNPs were placed on silicon wafer and allowed to air dry before examination. UV-Vis spectrum was performed for the prepared AuNPs. The spectrum shows a $\lambda_{max}$ at 531 nm characteristic of spherical AuNPs (FIG. 2) [14]. Scanning Electron Microscope (SEM) image (FIG. 3A) was analyzed by (*Image J* 1.4 *software Wayne Rasband, National Institutes of Health, USA*. http://_rsb.info.nih.gov/ij/java 1.6.0_05). The particles had an average diameter of about 30 nm and spherical in shape (FIG. 3B).

Isolation of Nucleic Acid from Serum

Serum Sample Collection.

Serum samples were collected from healthy volunteers (n=38) and from chronic HCV patients (n=48). Rapid HCV test was performed on all the samples. All positive samples had elevated ALT and AST levels. All samples were negative for hepatitis B surface antigen and hepatitis B antibody.

Extraction of HCV RNA.

Extraction of HCV RNA from serum samples was performed using SV total RNA isolation System (Promega; Cat. No. Z3100) according to the modified manufacturer's protocol for HCV RNA isolation [16].

Real-Time RT-PCR.

Real-time RT-PCR was performed using AgPath ID One Step RT-PCR kit (cat #AM1005; Ambion) [17] according to manufacturer's protocol. To 16.5 µl master mix, 8.5 µl of the extracted HCV RNA was added and amplification was performed using Stratagene (Mx3005P) under the following cycling conditions: 1 cycle of 45° C. for 10 min, 1 cycle of 95° C. for 10 min followed by 45 cycles of 95° C. for 15 s and 60° C. for 45 s.

Colorimetric AuNP-Based Assay.

To 5 µL of the extracted HCV RNA, 5 µL of 2M Phosphate buffer was added followed by 30 µL of the positively charged AuNPs. The sample was mixed by pipetting and the color of the solution was observed within 5 minutes.

Example 2: Silica Nanoparticle Capturing Method

Colloidal Silica Nanoparticles: Synthesis and Functionalization.

Figure 5A:
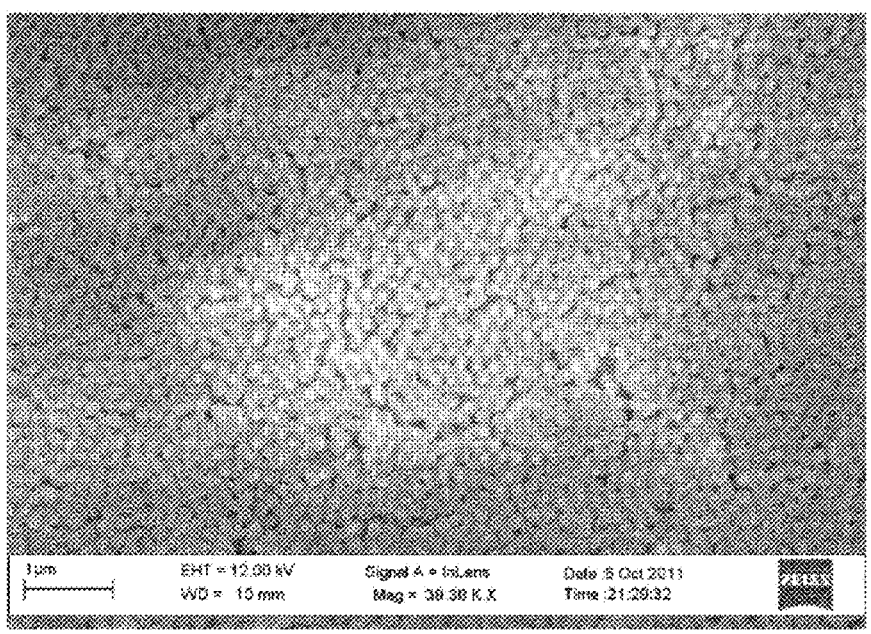
(FIG. 5A) SEM of the prepared silica nanoparticles.
Figure 5B:
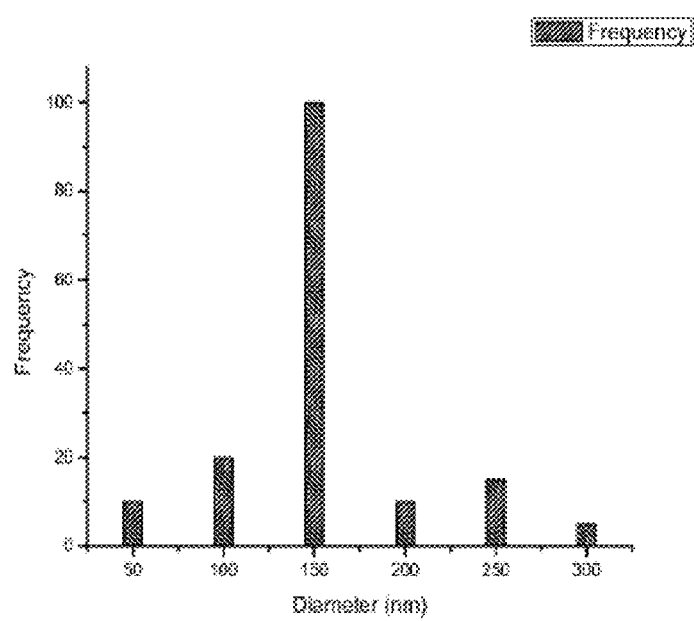
(FIG. 5B) Diameter calculation of the prepared silica nanoparticles.

HCV RNA was extracted using colloidal silica nanoparticles conjugated to an oligonucleotide specific to HCV RNA. Initially, 200 nm colloidal silica nanoparticles were synthesized with a modified stober method (modification was done in our lab). Briefly, in a beaker mix absolute ethanol, deionized water, concentrated ammonia and tetraethyl orthosilicate (TEOS), and stir at room temperature for about 1 hour. Then, the formed colloidal solution was centrifuged at 4000 rpm for 10 minutes, and the supernatant was discarded and the pellet was washed with absolute ethanol. This washing step was repeated for about 4 times or until no ammonia odor in the solution. The pellet was then dispersed in absolute ethanol and sonicated for about 5 minutes to remove any aggregates. The produced silica nanoparticles were examined using scanning electron microscope (SEM), to get the morphology and the diameter of the prepared silica nanoparticles (FIG. 5).

Figure 6A:
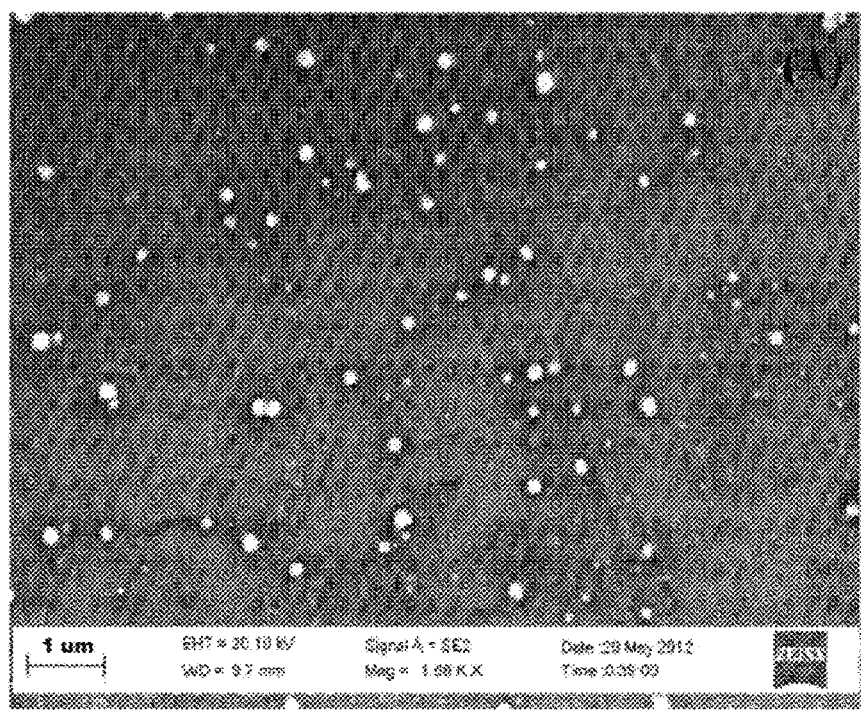
(FIG. 6A) SEM of the prepared magnetic nanoparticles.
Figure 6B:
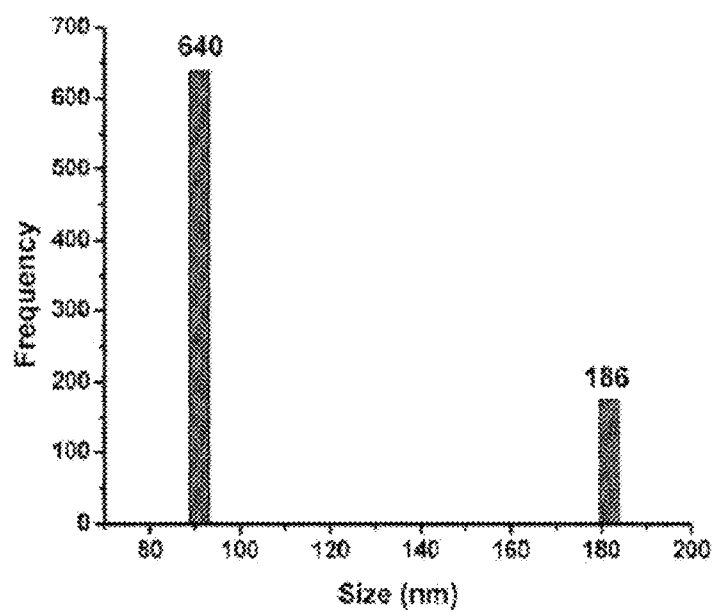
(FIG. 6B) Diameter calculation of the magnetic nanoparticles.
Figure 6C:
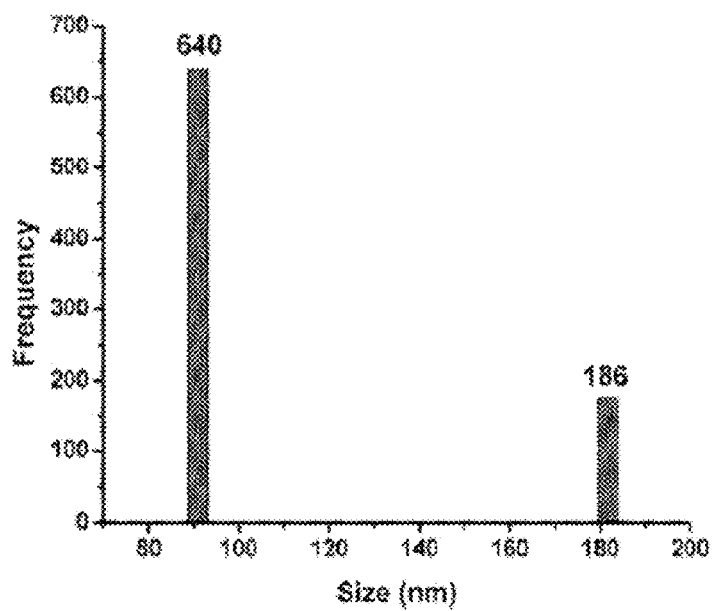
(FIG. 6C) FT-IR of magnetic nanoparticles functionalized with amino propyl tri-ethoxy silane (APES), The band at 583 $cm^{-1}$ corresponds to the Fe—O bond, the one at 1050 $cm^{-1}$ and 1380 $cm^{-1}$ corresponds to the vibrations of $SiOCH_2$ structure and Si—$CH_2$ scissoring vibrations respectively, while the N—H bending mode and stretching vibrations of the free amino groups are appeared at bands 1625 $cm^{-1}$ and 3436 $cm^{-1}$ respectively. Also, the anchored propyl group of the APTES is present at band 2923 $cm^{-1}$.

The prepared silica nanoparticles were functionalized with amino propyl trimethoxy silane (APMS) to introduce amino groups on the surface of the silica nanoparticles. Briefly, 1 ml of APMS was added to 20 ml of the prepared colloidal silica nanoparticles and stirred at room temperature for at least 2 hours, then the solution was centrifuged at 4,000 rpm for 10 minutes, and the supernatant was discarded and the pellet resuspended in phosphate buffer saline (PBS 1×). The number of silica nanoparticles per ml was calculated as previously described [18]. Briefly, one ml of the prepared silica colloidal solution was taken centrifuged, and the supernatant was discarded, then the pellet was dried till complete dryness. The dried pellet was then weighted in milligrams and from the volume taken (1 ml) and the weight obtained, concentration of the colloidal solution has been calculated which is 12 mg/ml. From FIG. 6 the diameter of the silica nanoparticles was measured to be about 150 nm. The weight of one particle equals volume of the particle*specific gravity (2.3), the volume equals $4/3\ \pi r3$, and the particles count equals concentration (12 mg/ml)/ weight of one particle equals 2.95125E+12 silica nanoparticles/ml.

Synthesis of Silica Probe.

A heterobifunctional cross linker (3-maleimidobenzoic acid N-hydroxyl succinimide, MBS) was used to prepare an HCV specific probe conjugated to silica nanoparticles. This linker has NHS ester at one end which reacts with primary amine groups to form stable amide bond; the other end has maleimide group which reacts with sulfhydryl groups. The cross linker binds to the amine functionalized silica nanoparticles through the NHS ester and to a thiolated HCV specific probe through the maleimide group. The thiol labeled probe was prepared as previously described [19, 20]. 10 mg of MBS dissolved in 1 mL dimethyl formamide plus 2.5 ml PBS and 2.5 ml of amino functionalized silica nanoparticles and mix at room temperature for at least 2 hours, and then purified by centrifugation, the thiol modified probe was added to the MBS conjugated silica nanoparticles and incubate at room temperature for at least 2 hours. The number of probes per one silica nanoparticle was calculated by first multiplying the number of moles of the probe by Avogadro's number, and then dividing the number of probes calculated by the silica nanoparticles count, and it was about 500 probes per one silica nanoparticle.

Extraction of HCV RNA from Clinical Samples Using the Prepared Silica Probes.

To 200 11.1 of patient sera, 200 µl of lysis buffer (Promega SV viral RNA) was added. After mixing by inversion, 50 µl Proteinase K was added and left to incubate for 10 min. The mixture was heated to 95° C. in a heat block for 2 min then 50 µl silica-probes was added and the reaction mixed for 1 hr. The mixture was centrifuged at 3000 RPM for 3 min and the pellet was washed twice with nuclease-free water. The HCV RNA was then eluted by heating at 95° C. for 5 min. The mixture was centrifuged and the supernatant contained the eluted RNA was separated. The extracted RNA was tested using both Real-time RT-PCR and the developed colorimetric AuNP-based assay.

Comparison Between Colorimetric AuNP-Based Assay and Real-Time RT-PCR.

HCV RNA extracted by the Promega kit or by the silica probe developed by the inventors was detected and quantified using Real-Time RT-PCR as described above. The assay developed by the inventors using positively charged AuNPs was performed on the samples extracted using the silica probe to detect HCV RNA. The color of the AuNPs colloidal solution of the negative samples remained red in color which indicates no nucleic acid was present in the sample.

On the other hand, the presence of HCV RNA in the positive samples lead to aggregation of the AuNPs and the color changed from red to blue (FIG. 4), the intensity of the blue color in positive samples was compatible with the viral load as quantified by Real-Time PCR. Of the 68 HCV positive samples, 63 samples gave blue color which indicates the presence of the HCV RNA, while no change in color occurred in 5 samples (False negative).

On the other hand, 56 out of 58 negative samples gave red color which indicates the absence of HCV RNA in addition to any other nucleic acid (high purity of the sample), while one sample only gave blue color due to AuNPs aggregation (False Positive). These results show that the cationic AuNP based assay has specificity of 96.5%, and a sensitivity of 92.6%.

Example 3: Magnetic Nanoparticle Capturing Method

Iron Oxide Magnetic Nanoparticles: Synthesis and Functionalization.

HCV RNA was extracted using homemade magnetic nanoparticles conjugated to an oligonucleotide specific to HCV RNA. First, 90 nm magnetic nanoparticles were synthesized as described elsewhere [21]. Typically iron (II) chloride and iron (III) chloride (1:2) were dissolved in nanopure water at the concentration of 0.25 M iron ions and chemically precipitated at room temperature (25° C.) by adding 1 M NaOH at a constant of pH 10. The precipitates were heated at 80° C. for 35 min under continuous mixing and washed four times in water and several times in ethanol. During washing, the magnetic nanoparticles were separated from the supernatant using a magnet, and the particles were finally dried in a vacuum oven at 70° C.

Amino functionalization of the prepared magnetic nanoparticles was done by amino propyl Trimethoxy silane (APMS) as described elsewhere [22]. Briefly, magnetic nanoparticles (1 g) were washed with 99.5% methanol and twice with Nanopure water and soaked in 10 mL of 3 mM APTMS solution in a toluene/methanol (1:1 v/v) mix. The suspension was then transferred into a three-necked flask with a water-cooled condenser and temperature controller with a nitrogen gas flow at 80° C. for 20 h under vigorous stirring. Silanization was found to occur at the surfaces of the particles bearing hydroxyl groups, which in the presence of an organic solvent results in the formation of an APTMS coating with a large density of amines. The particles were recovered by applying an external magnetic field after the silanization process and washed three times with methanol and dried at 50° C. in a vacuum oven.

Characterization of Magnetic Nanoparticles.

The prepared magnetic nanoparticles were characterized by SEM for size and particles distribution determination. Moreover, Fourier transform infrared spectroscopy (FT-IR) was used to record the IR spectra of the samples using potassium bromide (KBr) pellet technique.

Conjugation of HCV Specific Probe to the Amino Functionalized Magnetic Nanoparticles.

To prepare the magnetic nanoparticles conjugated to HCV RNA specific probe, heterobifunctional cross linker (3-maleimidobenzoic acid N-hydroxyl succinimide, MBS) was used that has NHS ester at one end that reacts with primary amine groups forming stable amide bond, and the other end has maleimide group that reacts with sulfhydryl groups forming stable thioether linkage. Functionalization procedures were done as following: Firstly, the disulfide labeled probe was prepared as previously described [19, 20]. Briefly, disulfide cleavage of the probe was done by lyophilization of 10 nmol of the probe and then resuspended in 100 ul of 0.1 M dithiothrietol (DTT) prepared in disulfide cleavage buffer (170 mM phosphate buffer, pH=8). The solution was wrapped in foil and let to stand at room temperature for 2-3 h with occasional vortexing. Desalting of the freshly cleaved probe was done using Nap-5 column (illustra NAP-5 (GE Healthcare) according to the manufacturer's instructions. UV-visible spectrophotometer was used to determine the purified probe concentration. Secondly, the amine functionalized magnetic nanoparticles were washed with Dimethyl sulfoxide (DMSO) for 2 times, the wash discarded, then MBS cross linker dissolved in DMSO was added to the washed magnetic nanoparticles The mixture was allowed to mix on a roller shaker for about 1 hour at room temperature. Then, the nanoparticles were washed with DMSO twice followed by coupling buffer (100 mM phosphate buffer and 0.2 M sodium chloride, pH=7) twice. Then, the particles were resuspended again in coupling buffer and the cleaved probe were added to the suspended particles and allowed to react on a roller shaker overnight. Finally, the supernatant was removed and the magnetic nanoparticles functionalized with HCV RNA specific probe were resuspended in storage buffer (10 mM phosphate buffer, 0.1 M sodium chloride, pH=7.4).

Extraction of HCV RNA from Clinical Samples Using the Prepared Probes.

To employ specificity and selectivity of the developed AuNP assay for a specific viral RNA/DNA, HCV RNA specific probe conjugated to magnetic nanoparticles was used for HCV RNA capture after virion lysis and digestion of the proteins in patient sera. In a 1.5 ml microcentrifuge tube, 100 ul of the magnetic nanoparticles conjugated to HCV specific probe was taken and washed twice with the assay buffer (10 mM phosphate buffer, 150 mM sodium chloride, pH=7.4) and then the modified magnetic nanoparticles were resuspended in 50 ul assay buffer.

In another 1.5 ml microcentrifuge tube 200 µl of patient sera was added to 200 µl of lysis buffer to break down the viral envelope. After mixing by inversion, 50 µl Proteinase K was added to digest the serum proteins and left to incubate for 10 min. Then, the mixture was centrifuged for 10 minutes at 14,000 rpm and the supernatant was taken and mixed with 300 ul of iso-propanol. Then, the resuspended magnetic nanoparticles were added to the previous mixture and heated at 90° C. for 2 minutes to denature the target RNA. The mixture was shaken at a temperature ~15° C. below the melting point of the conjugated probe for 45 minutes. Then, the tubes were placed on magnet until all solutions were clear and the supernatant were removed. Then, the particles were washed twice with washing buffer (60 mM potassium acetate, 10 mM Tris-HCl, 60% ethanol, pH=7.5). Supernatant was removed between each wash with the help of magnet. Elution was done by adding 50 µl DEPEC—Water, and heated at 95° C. for 2 minutes. The tubes were placed on magnet until all solutions were clear and the eluted HCV RNA was transferred to new RNase free tube. After HCV RNA extraction the colorimetric gold nanoparticles based assay was performed as described before.

HCV RNA Capturing.

One hundred twenty six samples were used in this study: 68 samples from HCV positive subjects and 58 samples from healthy individuals. Each sample was divided and each part was subjected to extraction by one of two different methods: (i) by use of an SV total RNA isolation kit or (ii) by use of the developed silica and/or magnetic probe. The presence of the HCV RNA in the positive samples and the absence of HCV RNA in the negative samples extracted by the silica probe were confirmed with Real-Time PCR and compared with the samples extracted by the promega kit. The concordance between RNA extraction by the promega kit and the RNA extraction by the silica and/or magnetic probe was 100%, (which means that the developed silica and/or magnetic probe could be used alone for HCV RNA extraction without the need of any other commercial extraction kit. Moreover, the same principle can be used in extraction and purification of any other nucleic acid and/or protein by simply replace the HCV RNA specific probe with the other target specific molecule (e.g. antibodies, lectins, probes . . . etc), therefore the developed HCV RNA extraction method by the silica probe could be expanded to be used in many other targets. The main aim for capturing the HCV RNA capturing is to increase the purity of the sample from any other nucleic acids (DNA or RNA) that may interfere with the assay results and thus allowing an increase in assay specificity.

Other Applications.

The inventors have developed a novel colorimetric solution-phase cationic AuNP-based assay for the direct detection of unamplified RNA/DNA. This method has been exemplified using HCV RNA extracted from clinical specimens as a model nucleic acid. The developed assay is not complex because it simply requires adding cationic AuNPs solution to the target molecule (e.g., extracted RNA in presence of phosphate buffer, rapid (about 5 min), sensitive, cost-effective, and can be easily automated. Conveniently, the developed assay can be used as a platform for the detection of any RNA and/or DNA in solution form. In other words, if a specific nucleic acid extraction method is available for any nucleic acid to be determined; this assay provides an easy, simple and rapid way for its analysis.

This method provides a foundation for development of other silica-probe based extraction methods for extraction of specific kinds of nucleic acids, such as HCV RNA. This assay can be practiced quantitatively since the intensity of the blue colour produced by aggregation of gold and/or silver nanoparticles reflects the number of RNA/DNA molecules present in the extracted sample and corresponds to factors such as bacterial or viral load. Based on the disclosure above one of skill in the art could determine the qualitative or quantitative detection limit of an assay for a particular kind of nucleic acid, its linear range, accuracy and precision.

REFERENCES FOR PART 1

1. Radwan, S. H. and H. M. Azzazy, Gold nanoparticles for molecular diagnostics. Expert Rev Mol Diagn, 2009. 9(5): 511-24.
2. Cao R, et al., Naked-eye sensitive detection of nuclease activity using positively-charged gold nanoparticles as colorimetric probes. Chem Commun., 2011. 47(45): 12301-12303.
3. Kim J W, et al., An operationally simple colorimetric assay of hyaluronidase activity using cationic gold nanoparticles. Analyst, 2009. 134(7): 1291-1293.
4. Ma Z, et al., Optical DNA detection based on gold nanorods aggregation. Anal chem Acta, 2010. 673(2): 179-184.
5. Sun, Y., et al., Microarray gene expression analysis free of reverse transcription and dye labeling. Anal Biochem, 2005. 345(2): 312-9.
6. Hsiao C R and C. C H, Characterization of DNA chips by nanogold staining. Anal Chem, 2009. 389(2): 118-123.
7. WHO http://www.who.int/vaccine_research/diseases/hepatitis_c/en/ [last accessed on Jul. 22, 2010].
8. Gourley, P. L., Brief overview of BioMicroNano technologies. Biotechnol Prog., 2005. 21 (1): 2-10.
9. Tolaymat, T. M., et al., An evidence-based environmental perspective of manufactured silver nanoparticle in syntheses and applications: A systematic review and critical appraisal of peer-reviewed scientific papers. science of the total environment, 2009. 408: 999-1006.
10. Sui, Z., et al., Capping effect of CTAB on positively charged Ag nanoparticles. Physica E.: Low-dimensional systems and nanostructures, 2006. 33(2): 308-314.
11. Khan, Z., et al., Preparation and characterization of silver nanoparticles by chemical reduction method. Colloids and Surfaces B: Biointerfaces, 2011. 82: 513-517.
12. Siliu Tan, et al., Synthesis of positively charged silver nanoparticles via photoreduction of AgNO3 in branched Polyethyleneimine/HEPES solutions. langmuir, 2007. 23(19): 9836-9843.
13. Kima, J., S. W. Kang, and Y. S. Kang, Partially positively charged silver nanoparticles prepared by p-benzoquinone. Colloids and SurfacesA: Physicochem. Eng. Aspects, 2008. 320: 189-192.
14. Huang X: Gold Nanoparticles Used in Cancer Cell Diagnostics, Selective Photothermal Therapy and Catalysis of NADH Oxidation Reaction. Laser Dynamic Laboratory, School of Chemistry and Biochemistry Doctor of philosophy, 234 pages (2006).
15. Jain, P. K., et al., Calculated Absorption and Scattering Properties of Gold Nanoparticles of Different Size, Shape, and Composition: Applications in Biological Imaging and Biomedicine. J. Phys. Chem. B, 2006. 110(14): 7238-7248.
16. Link, S. and M. A. El-Sayed, Spectral Properties and Relaxation Dynamics of Surface Plasmon Electronic Oscillations in Gold and Silver Nanodots and Nanorods. J. Phys. Chem. B, 1999. 103(40): 8410-8426.
17. Wagner, V. et al., The emerging nanomedicine landscape. Nat Biotechnol, 2006. 24(10): 1211-7.
18. Nakamura, M., M. Shono, and K. Ishimura, Synthesis, characterization, and biological applications of multifluorescent silica nanoparticles. Anal Chem, 2007. 79(17): 6507-14.
19. Rosi, N. L., et al., Oligonucleotide-modified gold nanoparticles for intracellular gene regulation. Science, 2006. 312: 1027-1030.
20. Haley D Hill and C. A. Mirkin, The bio-barcode assay for the detection of protein and nucleic acid targets using DTT-induced ligand exchange. Nature Protocols 2006. 1: 324-335.
21. Kouassi, G. K., J. Irudayaraj, and G. McCarty, Activity of glucose oxidase functionalized onto magnetic nanoparticles. Biomagn. Res. Technol., 2005. 3(1): 1.
22. Kouassi, G. K. and J. Irudayaraj, Magnetic and gold-coated magnetic nanoparticles as a DNA sensor. Anal. Chem, 2006. 78(10): 3234-41.

PART 2: DETAILED DESCRIPTION OF THE INVENTION

Anisotropic Silver Nanoparticles.

The synthesis of anisotropic silver nanoparticles is a time-consuming process and involves the use of expensive toxic chemicals and specialized laboratory equipment. The presence of toxic chemicals in the prepared anisotropic silver nanostructures hindered their medical application. The inventors have developed a fast and inexpensive method for the synthesis of three dimensional hollow flower-like silver nanostructures without the use of toxic chemicals. In this method, silver nitrate was reduced using dextrose in presence of trisodium citrate as a capping agent. Sodium hydroxide was added to enhance reduction efficacy of dextrose and reduce time of synthesis. The effects of all four agents on the shape and size of silver nanostructures were investigated. Robust hollow flower-like silver nanostructures were successfully synthesized and ranged in size from 0.2 μm to 5.0 μm with surface area between 25-240 $m^2$/g. Changing the concentration of silver nitrate, dextrose, sodium hydroxide, and trisodium citrate affected the size and shape of the synthesized structures, while changing temperature had no effect. The disclosed method is simple, safe, and allows controlled synthesis of anisotropic silver nanostructures, which may represent promising tools as effective antimicrobial agents and for in vitro diagnostics. The synthesized hollow nanostructures may be used for enhanced drug encapsulation and sustained release.

Particular embodiments of the invention are described below: Methods that control of size and morphology of synthesized nanostructures that do not require the use of particular polymers, surfactants and/or special laboratory equipment. These methods are used for synthesizing novel silver nanostructures having the following characteristics:

sizes ranging from 0.17 to 7 µM having distributed pores ranging in size from 10 to 20 nm and that have a 3 dimensional ("3d") flower-like structure with multilayer hollows, rough surfaces, external channels and distributed interior hollows;

unique flower like silver structures with multi layer of hollows in the range of 3-15 layers, surface roughness ranged from 10-200 nm, more rough surface, with larger holes (10-20 nm in width and 200-300 nm in length), highly external channels in the range of 1-4 channels surrounding silver structures with size ranging between 0.2-3.0 µM. Likewise 3d flower-like silver structures with size in the range of 0.25-2.5 µM with more multi layers (16-30 layers), surface roughness ranged from 250-400 nm, with larger holes ranged from 50-200 nm, highly external channels ranged from 5-10 channels surrounding silver particles.

unique 3d shell-like silver structures with little pores ranged between 5-30 nm, rough surface (180-300 nm), highly external arms ranged from 3-9 arms surrounding particles, having size ranging between 0.15-1 µM.

unique scaffold like silver structures having size ranging between 2-7 µM with highly inter connected pores ranging between 50-100 nm width and 100-500 nm length;

unique roll fiber twin like silver structures having size ranging between 0.15-1 µM with multi hard external arms on the surface complete shelled the particles;

unique 3d pores spherical silver structures have size in the range 0.6-5 µM of with well distributed external pores on the surface ranges between 50 nm-300 nm;

unique 3d pores spherical silver structures spongy like with size in the range of 0.3-2 µM with well interconnected pores in the range of 20-100 nm;

flower like with multi external interacted layers of hollows, branched rough edges silver nanostructures with size in the range of 0.3-1.5 µM with well controlled size and dispersion;

flower-like silver structures with multi layer of paper, hollows like cores, soft surface silver nanostructures with size in the range of 0.2-1 µM with well controlled size and dispersion;

trees with multi branched edges like arms like silver nanostructures with size in the range of 2-6 µM with well controlled size and dispersion;

dendrimer silver nanostructures with size in the range of 0.7-2 µM with well controlled size and dispersion;

flower silver structures with more internal hollows, rough surface silver nanostructures with size in the range of 0.24-1.5 µM with well controlled size and dispersion;

cubes silver structures with size in the range of 0.1-1 µM with well controlled walls and edges;

pyramidal silver structures with size in the range of 0.05-2 µM with well controlled walls, edges and soft surface;

bibode silver structures with size in the range of 50-200 nm with soft surface;

triangular silver structures with size in the range of 0.1-1 µM;

octahedral multi layer silver structures with size in the range of 100-400 nm;

octahedral multi layer, with pores on the surface silver structures with size in the range of 100-300 nm;

ribbed like silver structures with size in the range of 0.3-1 µM; multi ribbed with cubes decorated on the surface silver structures with size in the range of 100-600 nm;

octahedral with cube decorated on the surface silver structures with size in the range of 0.2-1 µM;

silver stars with size in the range of 0.1-4 µM and with soft branched arms and hole as core like;

silver stars with size in the range of 0.15-3 µM and with soft and rough, branched, more layer of arms and hole as core like;

silver flower structures with size in the range of 100-400 nm with soft, more layers of arms;

silver myriad dendrimer structures with size in the range of 0.5-2 µM, with highly branched arms and core like;

silver butterfly structures with size in the range of 0.6-1.5 µM and with highly branched arms like wings;

silver stars, flower structures with size in the range of 0.3-2 µM and by incorporation of polymers with TSC and using UV irradiation; and silver stars, flower structures with size in the range of 0.2-1 µM and by incorporation of polymers with TSC and without using of UV irradiation.

Synthesis of Anisotropic Silver Structures.

The anisotropic silver structures silver nanostructures, and microstructures with control in size, shape were synthesized by chemical reduction of silver nitrate with dextrose in presence of trisodium citrate and sodium hydroxide (NaOH). Dextrose acts as reducing agent, as capping agents TSC act only as capping material, NaOH acted enhance reduction efficacy of dextrose and as shape control.

Likewise, cubes, pyramidal, triangular, silver nanostructures, macrostructures, are prepared by incorporation of ascorbic acid with TSC, dextrose and NaOH. By the same way dextrose act as reducing agent, as capping agents TSC act only as capping material, NaOH acted enhance reduction efficacy of dextrose, Ascorbic acid and as shape control. The particles morphology, size were controlled by reaction condition include amount of TSC, $AgNO_3$, dextrose, ascorbic acid, and NaOH as will be demonstrated and discussed below. The methods demonstrated herein provide nanostructures, macrostructures with high uniformity in size, controllable size, morphology, large quantities, reproducibly and good solubility in various solvents. In addition to such method are fast, echo-friendly, and inexpensive, with lack of specially laboratory equipments and laboratory skills.

A round bottom glass flask (100 mL) were cleaned in aqua regia (3 parts HCl, 1 part $HNO_3$) and rinsed with DDI water and dried in the oven at 60° C. All the other glasses were should be cleaned by the same way.

The formulas included silver nitrate $AgNO_3$ (silver source), trisodium citrate salts, anhydrous (TSC) (shape control reagents), dextrose (reducing agents, shape controller), L-Ascorbic acid (ascorbic acid) as reducing agents, Sodium hydroxide pellets, 97% (NaOH) and DDI water as solvents all above reagents were provided from Sigma Aldrich and water provided from mille pore (Millipore Corporation, Billerica, Mass.) with a resistivity of 18 MΩcm in our lab.

A solution of $AgNO_3$ were prepared by dissolved appropriate amount of $AgNO_3$ in DDI water with final concentrations of 0.001-2.0 M and 0.001-0.1 mM, and vortex for 1.5 min to complete dissolution and covered with aluminum fuel to protect from light. A solution of TSC was prepared by dissolving appropriate amount of TSC in DDI water with final concentrations of 0.001-2.0M and vortex for 1.5 minute to complete dissolution. A solution of Ascorbic Acid were prepared by dissolved appropriate amount of Ascorbic Acid in DDI water with final concentrations of 0.3-3.0 M and vortex for 2 min to complete dissolution and covered with aluminum fuel to protect from light. A solution of dextrose were prepared by dissolved appropriate amount of dextrose in DDI water with final concentrations of 0.001-2.0 M and vortex for 2 min to complete dissolution and cover with aluminum fuel to protect from light. A solution of NaOH was prepared by dissolved appropriate amount of NaOH in DDI water with final concentrations of 0.001-5.0 M and vortex for 2 min to complete dissolution. All the above reagents should be stored in sterilized Falcon tubes.

Synthesis of Nanoparticles Having 3d Flower-Like Morphology.

The 3d flower like morphology with distributed interior hollow structures; branched edges are synthesized by the chemical reduction of silver nitrate in aqueous phase. Briefly 0.001-2.0 M $AgNO_3$, 0.001-2.0M TSC solution, 0.3-3.0M of dextrose added to 15 mL DDI, then added various concentration of NaOH 0.001-5.0 M, stirred at room temperatures the color change immediately to deep gray or green, deep yellow depended on the reaction condition after the color changed, the solution is stirred for an additional 5 minutes, and stirrer turn off. The particles were collected by centrifugation at 1400 rpm for 10 minute, the supernatant was discarded and precipitate re-suspended in DDI water; the process was repeated three times to remove excess dextrose.

Example 1

Figure 8:
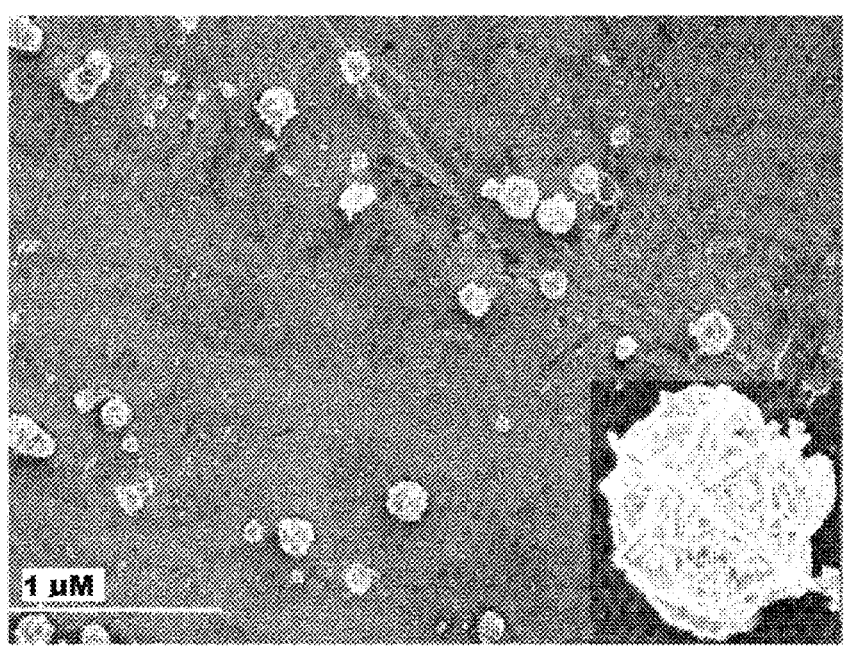
FIG. 8 shows SEM photographs of 3d flower-like silver structures with hollow multi layers (3-15 layers), surface roughness (10-200 nm), external channels (1-4) surrounding the particles.

The 3d flower-like silver structures with multi layer of hollow, rough surface, external channels surrounded particles were synthesized according to the above condition but using 0.2 mL of $AgNO_3$, 0.4 mL of TSC, 0.4 mL of dextrose added to 15 mL of DDI water; stirring at room temperature the color turned to deep yellow immediately after addition of 100 μL of NaOH then the solution is stirred for an additional 5 min, stirrer turned off and samples collected by centrifugation as mentioned above (FIG. 8).

Example 2

Figure 9:
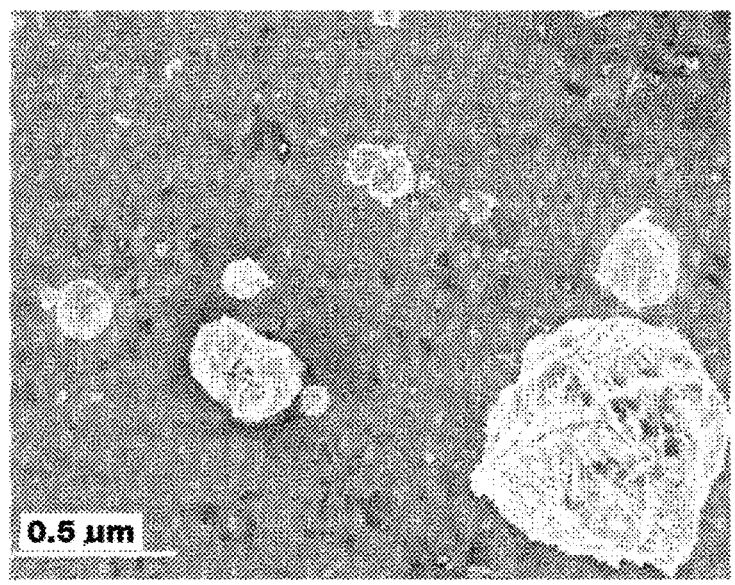
FIG. 9. SEM of 3d flower-like silver structures with more multi layer (16-30 layers) of hollow, surface roughness (250-400 nm), with larger holes (50-200 nm), highly external channels (5-10) surrounding the particles.
Figure 10A:
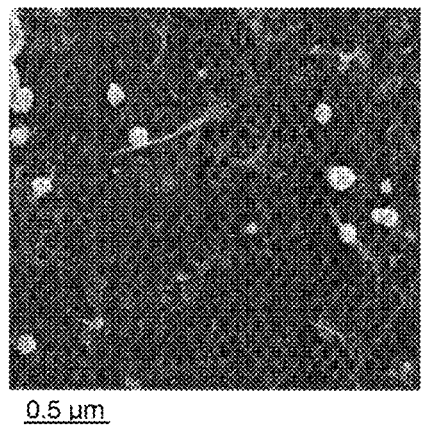
FIG. 10. 3D scaffold fibers like (FIG. 10B), flakes (FIG. 10C), and cluster (FIG. 10D) Silver structures before centrifugation (FIG. 10A). 3D scaffold like with hollow layer (10-50 nm in width and 100-500 nm length) and rough surface (150-500 nm). Silver flakes like 10-50 nm in width and 20-200 nm length.
Figure 10B:
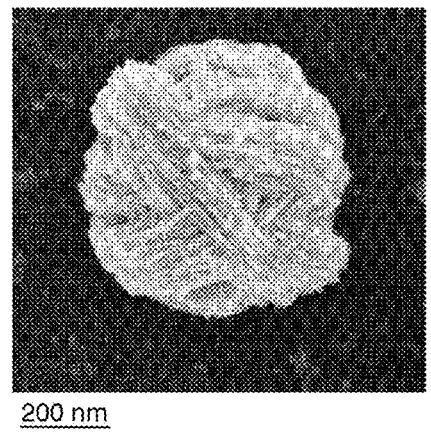
Figure 10C:
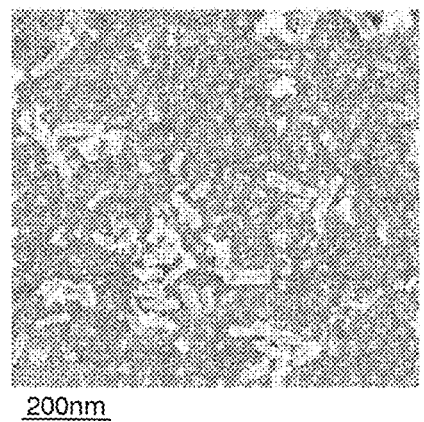
Figure 10D:
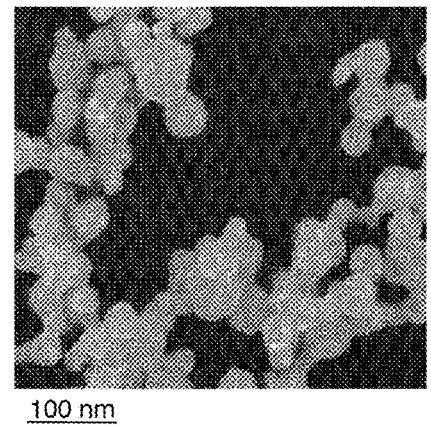
Figure 11:
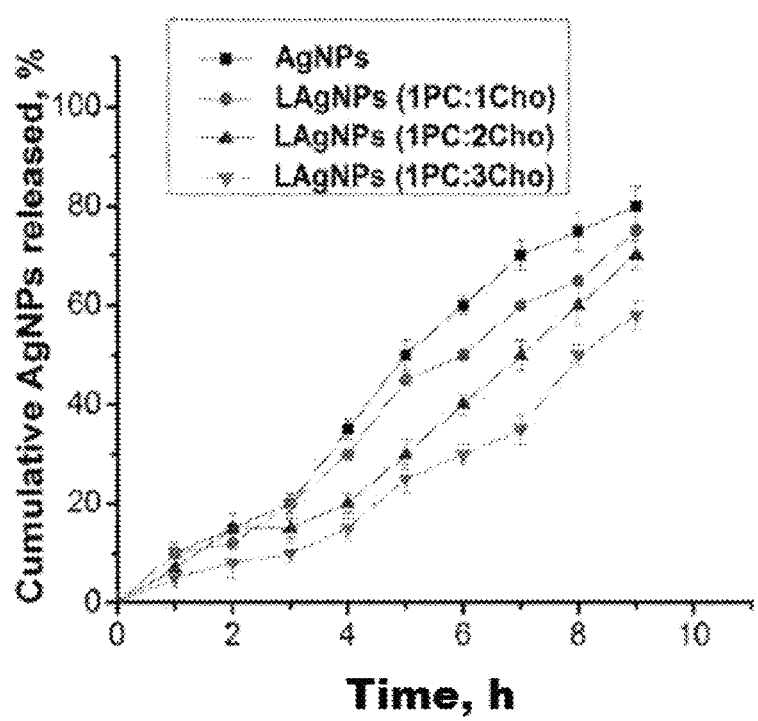
FIG. 11. Cumulative release of AgNPs over time from LAgNPs prepared with 1:1, 1:2, or 1:3 molar ratios of PC:Cho and 1 molar ratio of AgNPs. Diffusion of free AgNPs through cellulose membrane was used as a control.
Figure 12A:
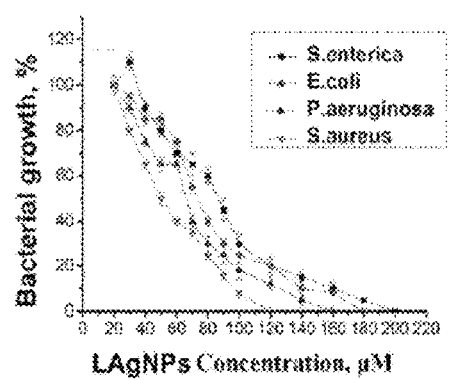
FIG. 12. Antimicrobial effects of nanoliposomes (FIG. 12C), free AgNPs (FIG. 12B), and LAgNPs (FIG. 12A) against four different bacterial strains. In all experiments, bacterial growth was determined by reading absorbance at 600 nm after 24 h of treatment. Nanoliposomes used were prepared using 1PC:3 Cho.
Figure 12B:
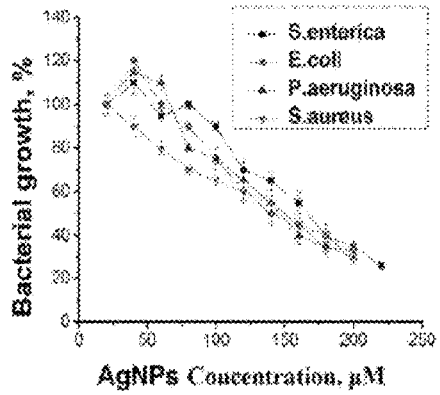
Figure 12C:
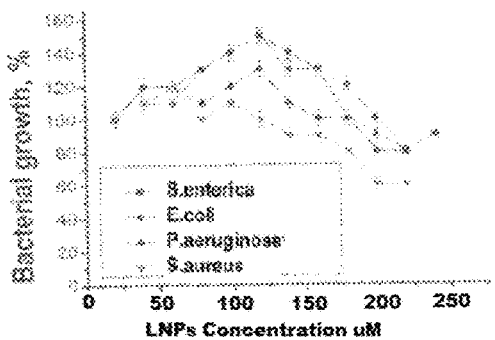

The 3d flower-like silver structures with more multilayer of hollow, more rough surface, with larger hollows, highly external channels surrounded particles were synthesized according above condition but using 0.2 mL of $AgNO_3$, 0.4 mL of TSC, 0.4 mL of dextrose added to 15 mL of DDI water, stirring at room temperatures the color turn to gray immediately after addition of 250 μL of NaOH then the solution is stirred for an additional 5 minutes, stirrer turned off and samples collected by centrifugation as mentioned above (FIG. 9).

Example 3

The 3D scaffold fibers like, flakes, and cluster silver structures little hollow pores, more rough surface, highly external arms surrounded particles were synthesized according above condition but using 1 mL of $AgNO_3$, 1 mL of TSC, 1 mL of dextrose added to 15 mL of DDI water, stirring at room temperatures the color turn to green immediately after addition of 50 μL of NaOH then the solution is stirred for an additional 5 min, stirrer turned off and samples collected by centrifugation 3 times at 8,000, 12,000, and 14,000 rpm, respectively.

Example 4

The 3d scaffold-like silver structures with little pores hollow, more rough surface, were synthesized according above condition but using 0.3 mL of $AgNO_3$, 0.6 mL of TSC, 0.6 mL of dextrose added to 15 mL of DDI water, stirring at room temperatures the color turn to deep green immediately after addition of 100 μL of NaOH then the solution is stirred for an additional 5 minutes, stirrer turned off and samples collected by centrifugation as mentioned above.

Example 5

The 3d roll fiber twin-like silver structures with little pores hollows, more rough surface, were synthesized according above condition but using 0.3 mL of $AgNO_3$, 0.6 mL of TSC, 0.6 mL of dextrose added to 15 mL of DDI water, stirring at room temperatures the color turn to deep green immediately after addition of 250 μL of NaOH then the solution is stirred for an additional 5 min, stirrer turned off and samples collected by centrifugation as mentioned above.

Example 6

The porous spheroid silver structures with little pores hollow, more rough surface, were synthesized according above condition but using 1 mL of $AgNO_3$, 1 mL of TSC, 1 mL of dextrose added to 15 mL of DDI water, stirring at room temperatures the color turn to deep green immediately after addition of 200 μL of NaOH then the solution is stirred for an additional 5 minutes, stirrer turned off and samples collected by centrifugation as mentioned above.

Example 7

The porous spherical sponge-like silver structures with high inter connected pores, more rough surface, were synthesized according above condition but using 1 mL of $AgNO_3$, 1 mL of TSC, 1 mL of dextrose added to 15 mL of DDI water, stirring at room temperatures the color turn to deep green immediately after addition of 100 μL of NaOH then the solution is stirred for an additional 5 minutes, stirrer turned off and samples collected by centrifugation as mentioned above.

Example 8

The 3d flower-like silver structures with multi external interacted layers of hollow, branched rough edges were synthesized according to above condition but using 1 mL of $AgNO_3$, 1 mL of TSC, 1 mL of dextrose added to 10 mL of DDI water, added 50 μL of NaOH stirring with heating up to 100° C. the color turn to yellow to deep brown immediately after 5 min then the solution is stirred till to cooling to room temperatures and stirrer turned off and samples collected by centrifugation as mentioned above.

Example 9

The flower like silver structures with multi layer of paper, hollow-like cores, soft surface, were synthesized according to above condition but using 2.0 mL of $AgNO_3$, 2 mL of dextrose, stirring at room temperatures the color turn to deep yellow immediately after addition of 20 μL of NaOH then the solution is stirred for additional 10 min samples collected by centrifugation as mentioned above.

Example 10

The treelike silver structures with multi branched edges like arms were synthesized according to above condition but using 1 mL of AgNO$_3$, 2 mL of dextrose, added to 10 mL DDI water, then added 100 μL of NaOH stirring with heating up to 100° C. the color turned to yellow to deep gray with precipitates after 3 min then the solution was allowed to cool to room temperature with stirring and samples collected by centrifugation as mentioned above.

Example 11

The flower-like silver structures with more wide internal hollow like core, multi-edge like arms were synthesized according to above condition but using 2 mL of AgNO$_3$, 1.0 mL of TSC, 1.0 mL of dextrose, then added 50 μL of NaOH and stirring with heating up to 100° C. the color turned to yellow to deep yellow after 5 min then the solution was stirred till cooling to room temperature and samples collected by centrifugation as mentioned above.

Example 12

The dendrimer silver structures were synthesized according to above conditions but using 0.5 mL of AgNO$_3$, 0.5 mL of dextrose, added to 5.0 mL of DDI water, then added 100 μL of NaOH with stirring at room temperature the color turned to yellow to deep gray and a precipitate was formed immediately, then the solution was stirred for additional 5 min and samples collected by centrifugation as mentioned above.

Example 13

The unique flower silver structures with more internal hollow, rough surface were synthesized according to above conditions but using 1.0 mL of AgNO$_3$, 1.0 mL of TSC, 1.0 mL of dextrose, then added 50 μL of NaOH, then stirring with heating up to 100° C., the color turned to yellow to deep gray then the solution was stirred till cooling to room temperature, and samples collected by centrifugation as mentioned above.

Example 14

The cube silver structures were synthesized according to above condition but using 0.4 mL of AgNO$_3$, 0.4 mL of dextrose, 0.4 mL of TSC, added to 5 mL of DDI water, then added 200 μL of ascorbic acid, then added 200 μL of NaOH and stirring at room temperature the color turned to yellow to deep gray immediately, then the solution was stirred for additional 5 min and samples collected by centrifugation as mentioned above.

Example 15

The pyramidal silver structures were synthesized according to above condition but using 0.5 mL of AgNO$_3$, 0.5 mL of dextrose, added to 5.0 mL of DDI water, then added 300 μL of NaOH stirring at room temperature the color turned to yellow to deep gray and a precipitate formed immediately, then the solution was stirred for additional 5 min and samples collected by centrifugation as mentioned above.

Example 16

The bibode silver structures were synthesized according to above conditions but using 1.0 mL of AgNO$_3$, 1.0 mL of dextrose, then added 150 μL of NaOH and stirring at room temperature the color turned to deep gray immediately, then the solution was stirred for additional 5 min and samples collected by centrifugation as mentioned above.

Example 17

The triangular silver structures were synthesized according to above conditions but using 1.0 mL of AgNO$_3$, 1.0 mL of TSC, 1.0 mL of dextrose added 100 μL of NaOH stirring with heating up to 100° C. the color turned to yellow to deep gray immediately after 5 min then the solution was stirred till cooling to room temperature and samples collected by centrifugation as mentioned above.

Example 18

The octahedral multilayer silver structures were synthesized according to above condition but using 0.5 mL of AgNO$_3$, 0.75 mL of dextrose, then adding 300 μL of ascorbic acid, stirring at room temperature the color turn to deep gray immediately, then the solution was stirred for additional 5 min and samples collected by centrifugation as mentioned above.

Example 19

The octahedral multi layer, with pores on the surface silver structures were synthesized according to above condition but using 0.5 mL of AgNO$_3$, 0.75 mL of dextrose, then added 200 of ascorbic acid, stirring at room temperatures the color turned to deep gray immediately, then the solution was stirred for an additional 5 min and samples collected by centrifugation as mentioned above.

Example 20

The ribbed silver structures were synthesized according to above conditions but using 0.5 mL of AgNO$_3$, 0.75 mL of dextrose, then added 150 μL of ascorbic acid, stirring at room temperatures the color turn to deep gray immediately, then the solution was stirred for additional 5 min and samples collected by centrifugation as mentioned above.

Example 21

The synthesis of multi ribbed with cubes decorated on the surface silver structures was done according to above conditions but using 0.5 mL of AgNO$_3$, 0.75 mL of dextrose, then adding 100 μL of ascorbic acid, stirring at room temperatures the color turned to deep gray immediately, then the solution was stirred for an additional 5 min and stirrer turn off and samples collected by centrifugation as mentioned above.

Example 22

The synthesis of octahedral with cube decorated on the surface silver structures was carried out according to above conditions but using 0.5 mL of AgNO$_3$, 0.75 mL of dextrose, added to 10 mL DDI water, then adding 100 µL of ascorbic acid and 100 µL of NaOH directly after ascorbic acid and stirring at room temperature. The color turned to pale gray immediately, then the solution was stirred for an additional 5 min and samples collected by centrifugation as mentioned above.

Synthesis of Silver Stars, Flower, Myriad Dendrimer and Butterfly Structures.

Stars, flower, myriad dendrimer, butterfly silver structures fly have been synthesized by reduction of $AgNO_3$ in aqua's TSC solution, TSC with polymer solution by ascorbic acid at room temperature. Likewise reduction of $AgNO_3$ in aqueous TSC with polymers was achieved by UV and then by ascorbic acid. The particle morphology and size were manipulated by changing amounts of $AgNO_3$, TSC, and duration of UV irradiation.

Example 23

The silver stars with soft arms were synthesized by the chemical reduction of silver nitrate in aqueous phase. Briefly; 0.3 mL of 0.001-0.1 mM $AgNO_3$, 0.5 mL of a 0.0001-2.0M TSC solution were added to 10 mL DDI, followed by 100 µL of ascorbic acid (0.3-3.0 M) and stirred at room temperature. The color changed immediately to gray and the solution was stirred for an additional 5 min, and stirrer turn off. The varying amounts of TSC (0, 300, 400, 500, 600, 700, 800, 1100 µL) lead to formation of silver stars with soft arms.

Example 24

Silver stars with soft and rough, branched, more layer of arms and holes as core like were formed by the same conditions above but using (50, 100, 200, 300, 400, 500, 600, 700, 800 µL) of 0.001-0.1 mM $AgNO_3$ and using 0.5 mL of a 0.0001-2.0M TSC solution added to 10 mL DDI, then adding 100 µL of ascorbic acid 0.3-3.0M, and stirred at room temperature. The color change immediately to gray. After color change, the solution was stirred for an additional 5 min. The color changed faster by using higher amounts of $AgNO_3$.

Example 25

Silver flower structures were formed by the same condition above but using 50, 100, 150, 200, 250, or 300 µL of 0.3-3.0 M ascorbic acid added to 10 mL DDI containing 300 µL 0.001-0.1 mM $AgNO_3$ and using 0.5 mL of 0.0001-2.0M TSC solution, then stirred at room temperature. The color changed immediately to gray, the solution is stirred for an additional 5 min. The color changed faster by using higher amounts of ascorbic acid.

Example 26

Silver myriad dendrimer structures were synthesized by the same conditions above and varying the amounts of TSC and $AgNO_3$. Briefly 300, 200, or 100 µL of 0.0001-2.0 M TSC were added to 300, 200, or 100 µL of 0.001-0.1 mM $AgNO_3$; and 10 mL DDI then 100 µL of 0.3-3.0M ascorbic acid were added. After stirring at room temperature the color changed to gray then the solution was stirred for an additional 5 min. The color changed faster when higher amounts of TSC and $AgNO_3$ were used.

Example 27

Silver butterfly were synthesized by the same condition above but using 500 µL of 0.0001-2.0 M TSC and 300, 200, or 100 µL of 0.001-0.1 mM $AgNO_3$ with 10 mL DDI then adding 80, 100 and/or 150 µL of 0.3-3.0 M ascorbic acid. After stirring at room temperature the color changed to gray then the solution was stirred for an additional 5 min. The color changed faster when higher amounts of ascorbic acid and $AgNO_3$.

Example 28

Silver stars were synthesized by using 0.001-0.1 mM $AgNO_3$, 0.5 mL of a 0.0001-2.0M TSC, 0.3 mL of polymer solution (PEG, PVA, PEI,) added to 10 mL DDI, then subjected to 18 W ultraviolet light at wave length (430 nm) for 30 min. The color turned to gray gradually. After adding 100 µL of 0.3-3.0 M ascorbic acid at room temperature the gray color changed to deep gray immediately. The solution was stirred for an additional 5 min. PVA or PMMA have been used with TSC as morphology controlling gannet for synthesis of star like silver structures with branched arms. Briefly, 0.3 ml of polymer solution (PVA or PMMA) with mixed with $AgNO_3$, TSC and reduced with ascorbic acid with and without UV (Claim 15). The varied time of UV irradiation have noted effects on the size and morphology of the synthesized particles.

Example 29

Silver stars, were synthesized without UV irradiation by using 0.3 mL of a 0.001-0.1 mM $AgNO_3$, 0.5 mL of a 0.0001-2.0 M TSC, 0.3 mL of polymer solution such as (PEG, PVA, PEI) added to 10 mL DDI. 100 µL of 0.3-3.0M ascorbic acid was added and stirred at room temperature the gray color change gradually to deep gray immediately, after the color changed, the solution is stirred for an additional 5 min. PVA or PMMA have been used with TSC as morphology controlling gannet for synthesis of star like silver structures with branched arms. Briefly, 0.3 ml of polymer solution (PVA or PMMA) with mixed with $AgNO_3$, TSC and reduced with ascorbic acid with and without UV (Claim 15). The varied amount of TSC, $AgNO_3$, polymers have noted effects on the size and morphology of the synthesized particles.

Zeta potential for silver structures (Example 1-7 and 23-29) were measured with dynamic light scattering NANO ZS Malvern zeta sizer equipment (Worcestershire, UK), at 25° C., using a He—Ne laser of 633 nm wavelength and a detector angle of 173°. Four independent measurements were made for each sample as tabulated in table 1. The result clearly demonstrated that, the silver structures are coated with negative charge ranged between −33 and −65 which it is strong enough to protect it from aggregation. Therefore the presence of electrical charge on the surface of silver structures makes it a promising tool in clinical diagnostics.

Example 30

See "Controlled synthesis and characterization of hollow flower-like silver nanostructures"; attached to U.S. 61/594, 817 and published as Eid & Azzazy, International Journal of Nanomedicine 2012:7 1543-1550 (Mar. 19, 2012).

Only the polyol process was versatile for the synthesis of the following structures: spherical, cubes, pyramidal, hollow cubes, bars, rice-like, octahedral, beam and spheroid. Polyol method gives mixtures of structures and there is a need for separation of different structures by nanofiltration.

Methods using poly (lactic-co-glycolic) acid templates gave similar star-like structures to the method of the invention but were not observed to provide the same variety of different structures. The method also requires a polymer template with or without UV irradiation and generates large size of stars, with lack of size control.

The nanoparticles of the invention can be used in numerous different applications.

They may be further processed, for example, by application of a surface coating to modify their solubility in polar or nonpolar media. For many biological applications, the application of a polar surface coating would be advantageous to provide solubility in aqueous media or in biological fluids. Nanoparticles may be functionalized with particular molecules to target them to particular receptors or to track their distribution. Examples of such targeting moieties include antibodies, protein or nucleic acid ligands that bind to specific receptors or molecules, aptamers, or other tags such as radioactive agents, fluorescent dyes, or tags like (strept)avidin or biotin or nickel and histidine. Hollow nanoparticles or nanoparticles having hollow portions can be used as vessels for carrying or containing other molecules such as those useful for imaging, plasmonics, or biosensing.

Silver spherical nanoparticles have been encapsulated inside liposome nanoparticles to act as a sustained broad spectrum antibacterial agent. The kinetic release, cytotoxicity, and antibacterial against Gram negative and Gram positive Bactria namely; *Escherichia coli, Salmonella enterica, Pseudomonas aeruginosa*, and *Staphylococcus aureus* were investigated against as described in the paper [Sustained Broad Spectrum Antibacterial Effects of Nanoliposomes Loaded with Silver Nanoparticles]. Thee strains growth was inhibited by more than 80% upon usage of using 200-225 µM of silver nanoparticles. The results obviously revealed that, the silver nanoparticles are promising tools in antibacterial therapy and wound healing. The optical properties of the silver nanoparticles were investigated by UV—visible—NIR measurements (Perkin Elmer UV/Vis/NIR Win lab lambda 950, 950N6102502, UK) and Pro Raman-L Analyser (Enwave Optronics Inc. 18200 McDurmott Calif. 92614, USA). The spectrum of the silver structures exhibit all characteristic peaks corresponding to different modes of plasmon excitation of all structures. There is more than dominant one band, located at around 342-300 nm and with intensity ranged between 500-13,000 a.u. Therefore the ability of silver structures to located band in both UV and NIR makes it a promising tool in SERS, optical, electronic, sensors and plasmonic applications.

Example 31

Dextrose was used to reduce silver nitrate with heating to form spherical silver nanostructures. Briefly, the spherical morphology was synthesized by the chemical reduction of silver nitrate in aqueous phase. An amount of 0.001-2M $AgNO_3$ solution mixed with 0.1-2 mM of dextrose and stirred with heating the color change immediately to deep yellow. After the color changed, the solution is stirred for an additional 5 minutes, and stirrer turn off. The particles collected by centrifuge at 1400 rpm for 10 minute, the supernatant can be removed, precipitate are re-suspended in DDI water and repeat three time for remove excess of dextrose. The Silver particle having size in the range of 10-50 nm and particle size depended on the concentration of dextrose.

TABLE 1

Zeta potential for all silver structures samples 1-29.

| Examples | Zeta potential mV |
|---|---|
| 1 | −45 ± 2 |
| 2 | −35 ± 3 |
| 3 | −28 ± 3 |
| 4 | −55 ± 4 |
| 5 | −37 ± 2 |
| 6 | −44 ± 5 |
| 7 | −33 ± 4 |
| 23 | −65 ± 3 |
| 24 | −55 ± 2 |
| 25 | −48 ± 4 |
| 26 | −62 ± 5 |
| 27 | −59 ± 4 |
| 28 | −61 ± 3 |
| 29 | −48 ± 3 |

TABLE 2

Other Versatile Methods for Synthesis of Silver Nanoparticles:

| Methods | Reagents | Morphology of Structures | Reference |
|---|---|---|---|
| Citrate reduction | Materials: $AgNO_3$ 2-propanol $N_2O$ Sodium citrate (stabilizer) pH controller such as NaOH UV | Spherical, quasi sphere and, octahedral., wire and triangle | [1-7] |
| Polyol (ethylene glycol + PVP) | Materials $AgNO_3$ or $(CF_3COOAg)$ Ethylene glycol (solvent-reducing agent) PVP (stabilizer polymer). Reducing agent: NaBr $HNO_3$ NaHs with HCl $CuCl$, $FeCl_3$ formamide/ethanol | Spherical, wires, beam, rice, cubes, bars, bipyramid, beam, octahedron, cube, truncated octahedron, and tubes | [8-25] [26] |
| Light-Mediated Synthesis | Material: $AgNO_3$ Methoxy polyethylene glycol or photosensitive polymer as Template Ethanol solution Hyperbranched polyurethane UV Polyol reagent | Silver chains, polygonal plates, disk, wire, rods and octahedron, spherical | [7, 27-33] |
| Seed growth | Materials: $AgNO_3$ Sodium citrate, L-arginine, PVP $NaBH_4$ Ascorbic acid PtCl or other metal salt CTAB or BDAC or combination of two | rods, wire, branched, decahedron and cubes | [6, 30, 34-40] |

Example 32

AgNPs Encapsulated in Nanoliposomes as Effective Broad Spectrum Anti-Microbial Agents.

Nanoliposomes (<50 nm) were prepared using a modified reverse phase evaporation method and spherical dextrose-capped AgNPs were synthesized. The prepared liposome AgNPs (LAgNPs) were characterized and tested for their antibacterial effects. The size of LAgNPs is 25-80 nm. Release of AgNPs from nanoliposomes was sustained over 10 h. Complete growth inhibition of *Escherichia coli, Sal-* monella enterica, Pseudomonas aeruginosa, and Staphylococcus aureus was achieved using 180, 200, 160, and 120 µM, respectively, of LAgNPs. As shown below, LAgNPs exhibited sustained broad-spectrum antibacterial effects as compared to free AgNPs.

Synthesis of spherical silver nanoparticles. Silver nitrate ($AgNO_3$), dextrose, egg Phosphatidylcholine (PC), cholesterol (Cho), MacConckey agar medium, broth medium, agarized Czapek Dox, ethanol, chloroform, and sodium hydroxide (NaOH) were purchased from Sigma-Aldrich Chemie GmbH (Munich, Germany). HCl and $HNO_3$ were purchased from El-Gomhouria Co, (Cairo, Egypt). Double deionized water (DDI) was prepared using a Milli-Q™ system (Direct-Q 3, Model ZRQSOPOWW, Millipore Corporation, Billerica, Mass.) with a resistivity of 18 MΩcm.

AgNPs were synthesized by the chemical reduction of $AgNO_3$ in aqueous solution. Briefly, a round-bottom flask was cleaned thoroughly with aqua regia (3HCl: $1HNO_3$) then rinsed with DDI water. $AgNO_3$ (0.01-1.0 M) was added to 0.1-2.0 M dextrose solution and dissolved in water at room temperature. NaOH (0.001-0.2 mM) was added during stirring. The solution changed from colorless to yellow, brown or green depending on the amount of $AgNO_3$, dextrose, and NaOH. Following color change, the solution was stirred for an additional 5 min, centrifuged, and washed three times with DDI water to remove excess dextrose.

Nanoliposomes were prepared using PC and Cho with different molar ratios (1:1, 1:2, 1:3, 1:4, 1:5, and 1:6). The lipid components were dissolved in 5 mL of chloroform and ethanol mixture (6:1, v/v). The solvents were removed using a rotary evaporator (Buchi RE-111 Rotavapor, Brinkmann, Westbury, N.Y.) at 55° C., 25 rpm, and high vacuum which has resulted in a lipid thin film. The film was redissolved in 10 mL PBS, pH 7.4 and the mixture was vortexed for 2 min and then sonicated using a probe sonicator (Model GM 2200, Bandelin Electronic, Berlin, Germany) with heating to form vesicles. The undispersed vesicles (aggregates) were separated by filtration.

For the synthesis of LAgNPs, the thin films prepared above were rehydrated with 10 mL PBS, pH 7.4, containing AgNPs (5 nm). The mixture was vortexed and sonicated with heating and then incubated at room temperature for 3 h then filtered to remove aggregates and free unencapsulated AgNPs Mean particle size diameter and polydispersity index of nanoliposomes and LAgNPs were measured directly after synthesis, using photo correlation spectroscopy (Malvern Instruments Ltd, Worcestershire, UK).

The size and morphology of the synthesized nanostructures were studied using scanning electron microscope (SEM, LEO SUPRA 55; Carl Zeiss AG, Oberkochen, Germany) and transmission electron microscope (TEM, JEOL X100, Japan). Briefly, silver samples were mounted on silicon wafer coated with aluminum foil and left 2 hours to dry before imaging without sputter coating before SEM imaging at an accelerating voltage of 6 kV and magnification of 150-200 k X. Liposome samples were diluted with BPS and sonicated for 3 min then negatively stained with 2% uranyl acetate and mounted on TEM grids (carbon film supported by a copper grid) and allowed to dry for 2 h before imaging with TEM at an accelerating voltage ranging from 200-220 kV and magnification of 400-500 kX. The particle size was reported as the mean diameter of randomly selected structures.

The encapsulation efficiency of AgNPs in liposome was measured using atomic absorption spectrophotometer (Z-5000, Hitachi, Ltd., Tokyo, Japan). Briefly, 5 mL of the synthesized LAgNPs were injected into the system and the percentage of encapsulated AgNPs was calculated as follows: Silver loading=[(WT−WS)/WT]×100%, where WT is the total AgNPs added to the liposomes and WS is the portion of AgNPs that was not encapsulated and present in the supernatant after ultracentrifugation of LAgNPs.

Different preparations of LAgNPs (PC: Cho; 1:1, 1:2, 1:3) loaded with AgNPs (5 nm) were placed in cellulose dialysis bags. The bags were suspended in 30 mL of PBS, pH 7.4 where AgNPs were released into the buffer by diffusion. The release of AgNPs from the dialysis bags was observed over a period of 10 h. Each hour, 1 mL of the buffer was removed, and substituted with fresh buffer, to measure the concentration of released AgNPs using atomic absorption spectrophotometer equipped with silver lamp (Z-5000, Hitachi, Ltd., Tokyo, Japan). The instrument parameters were: 328.1 nm wavelength; 5 mA lamp current; 0.5 nm band pass, fuel flow rate 0.9-1.2 L/min, and temperature of 1100° C.

Escherichia coli, Salmonella, P. aeruginosa, and S. aureus were obtained from the department of Microbiology, VACSERA, Cairo, Egypt. Bacterial cells were cultured for 24 h on a MacConckey agar plates at 37° C. Colonies were resuspended in LB broth medium to achieve $10^6$ CFU/mL. This has been confirmed by measuring bacterial growth as optical density using a microplate plate reader (Tecn Infinity M200, CA, USA). Different concentrations of free AgNPs, LNPs (1PC:3Cho), or LAgNPs (1PC:3Cho:1AgNP) were added to the bacterial cultures. The bacterial growth in the culture medium was monitored by measuring the optical density at 700 nm.

The optical density of bacterial cultures, grown in 3 replicates with shaking at 37° C. with and without nanoparticles, was recorded every 60 min. The rate of bacterial growth was calculated using the following formula: [($N_t$−$N_o$)/$N_o$×100]; where $N_o$ was the OD of bacteria at time zero and $N_t$ is the OD of bacteria at the indicated time point.

Table A illustrates particle size and polydispersity of nanoliposomes and LAgNPs using photon correlation spectroscopy.

| PC:Cho | LNPs Size (nm) | Poly Dispersity | LAgNPs Size (nm) | Poly Dispersity |
|---|---|---|---|---|
| 1:1 | 240 ± 35 | 0.13 | 25 ± 4 | 0.01 |
| 1:2 | 270 ± 25 | 0.16 | 45 ± 5 | 0.015 |
| 1:3 | 310 ± 22 | 0.18 | 50 ± 3 | 0.02 |
| 1:4 | 340 ± 38 | 0.2 | 65 ± 1 | 0.04 |
| 1:5 | 410 ± 40 | 0.31 | 70 ± 3 | 0.05 |
| 1:6 | 450 ± 28 | 0.4 | 80 ± 5 | 0.07 |

*Same molar ratio of AgNPs was added to all PC/Cho preparations.

The LAgNPs size ranged between 25 to 80 nm and the size of nanoliposomes between 250 to 400 nm. The SD values for LAgNPs were calculated from four independent measurements. AgNPs of 5±1 nm were used. Nanoparticles showed low polydispersity indices (Table A). The dynamic light scattering showed a narrow size distribution of LAgNPs and poly size distribution for nanoliposomes. The encapsulation of AgNPs into nanoliposomes has led to long-term stability of LAgNPs.

The zeta-potential measurements of LAgNPs in solution ranged between −76 and −58 mV. After 3 months of storage at room temperature, measurements ranged between −69 and −45 mV. The persistence of the negative charge on the LAgNPs is indicative of their stability. The individual measurement results are shown in the supplementary data file.

The size and shape of the synthesized AgNPs were studied using SEM and particle size was reported as mean diameter of randomly selected structures. Spherical silver nanostructures with size in the range of 5±1 nm were observed. UV spectroscopy of AgNPs with maximum absorbance at 410 nm was performed. SEM (A-C) of nanoliposomes that were prepared by using 1:1, 1:2, and 1:3 molar ratio of PC:Cho were obtained. The particles have spherical morphology with particle size in the range of 250-400 nm.

The LAgNPs were analyzed by TEM and had spheroid shape with an average particle size between 25-90 nm. The addition of AgNPs to nanoliposomes may have contributed to the reduced size of nanoliposomes to less than 50 nm. The presence of charged AgNPs on the surface of nanoliposomes, supported by zeta potential measurements of AgNPs (−38 mV) and LAgNPs (−76 mV) (supplementary data), contributed to the stability of LAgNPs. This result is in agreement with previous reports which demonstrated that the presence of charged particles on the surface of nanoliposomes contribute to their stability [21-22]. Other groups used polymers or surfactants for the stabilization of liposomes [21-23].

The amounts of AgNPs encapsulated into six different formulas of nanoliposomes 1:1, 1:2, 1:3, 1:4, 1:5, and 1:6 (PC:Cho) were 60%, 75%, 88%, 80%, 78%, and 70%, respectively. The highest encapsulation (88%) was achieved using nanoliposomes of 1PC:3Cho.

The release of kinetic of free AgNPs from LAgNP prepared using 1:1, 1:2, and 1:3 PC:Cho was observed. The rate of release of AgNPs obeyed zero order kinetics with $r^2 > 0.96$. This is similar to the release patterns of other drugs from liposomes. About 80% of the free AgNPs diffused out of the cellulose bag after 10 h. Release of AgNPs was 76%, 64%, 58% from liposomes prepared using 1:1, 1:2, 1:3 PC:Cho, respectively. Therefore, sustained release of AgNPs was observed using LAgNPs (1PC:3Cho; 50 nm). Because of their high encapsulation efficiency and sustained release of AgNPs, LAgNPs prepared using 1PC:3Cho were tested for their anti-bacterial effects.

The antibacterial activity of LAgNPs prepared using 1PC:3Cho was assayed against four common bacterial species namely: *E. coli, Salmonella, P. aeruginosa,* and *S. aureus* and monitored by optical density measurements using a micro-plate reader. Different concentrations of the LAgNPs (20-225 μM) were tested. LAgNPs completely inhibited bacterial growth of *E. coli* (180 μM), *Salmonella* (200 μM), *P. aeruginosa* (160 μM), and *S. aureus* (120 μM). The growth of the above strains was not completely inhibited using 200-225 μM of AgNPs. Adding free nanoliposomes up to 150 μM had no effect on bacterial growth then the growth decreased by 30-45% upon increasing the concentration of nanoliposomes to 225 μM.

LAgNPs were more effective in inhibiting growth of Gram positive bacteria (*S. aureus*) as compared to Gram negative bacteria (*E. coli, S. enterica,* and *P. aeruginosa*). This may be due to the difference in the structure of the outer walls of Gram positive and negative bacteria.

Cytotoxicity of LAgNPs (0.05-0.3 mg/mL) to cultured human fibroblast cells was investigated using MTT assay. LAgNPs concentrations between 0.05 to 0.10 mg/mL were safe and did not affect cell viability; higher LAgNPs concentrations (0.2-0.3 mg/mL) were toxic to cultured fibroblasts.

This example shows for the first time that nanoliposomes loaded with AgNPs are useful as broad-spectrum antibacterial agents. The modified reverse phase evaporation method allowed the preparation of nanoliposomes with size between 25-80 nm without the need for high pressure homogenizer and extruder. Also, the AgNPs were prepared by a green method and all reagents used for preparation of nanostructures were non-toxic. The presence of AgNPs stabilized the nanoliposomes and led to narrow size distribution of LAgNPs. LAgNPs prepared with 1PC:3Cho demonstrated high encapsulation capacity and provided long term release of AgNPs. The results show the feasibility of using LAgNPs as a new generation of antibacterial agents for sustained killing of multiple kinds of bacteria. The LAgNPs are stable in pharmaceutical preparations and provide long term anti-bacterial effect at the infection site.

The invention claimed is:

1. A method for detecting a nucleic acid in a sample comprising:
    contacting a sample suspected of containing a nucleic acid with silica nanoparticles that are bound to a capture probe which binds to the nucleic acid, thereby binding the nucleic acid to the capture probe on the silica nanoparticles,
    eluting the captured nucleic acid from the silica nanoparticles,
    contacting the eluted nucleic acid with positively charged silver nanoparticles,
    determining the aggregation of the silver nanoparticles after contacting them with the eluted nucleic acid, and
    selecting a sample containing the nucleic acid when the silver nanoparticles aggregate in comparison with a control sample that does not contain the nucleic acid to be detected;
    wherein nanoparticle aggregation is determined colorimetrically by a color change from yellow which denotes substantially nonaggregated silver nanoparticles, to colorless or to white which denotes aggregated silver nanoparticles.

2. The method of claim 1 that comprises detecting a nucleic acid that is single-stranded DNA.

3. The method of claim 1 comprising detecting a nucleic acid that is single-stranded RNA.

4. The method of claim 1, wherein the nanoparticles are spherical or spheroidal and have an average diameter of 12 to 40 nm.

5. The method of claim 1, wherein the nanoparticles are spherical or spheroidal and have an average diameter of 15-18 nm.

6. The method of claim 1, wherein the nanoparticles are not spherical or spheroidal.

7. The method of claim 1, wherein the silver nanoparticles are rod-shaped having any aspect ratio.

8. The method of claim 1, wherein the nanoparticles are star-shaped.

9. A method for capturing at least one biological material of interest comprising contacting a sample comprising said material with silica nanoparticles, which comprise a ligand for the biological material, for a time and under conditions sufficient for the material to bind to the silica nanoparticles and eluting or recovering the biological material from the silica nanoparticles; wherein said method further comprises contacting the eluted or recovered biological material with silver nanoparticles;
    wherein said at least one biological material is HCV RNA,
    wherein the ligand for the biological material comprises a nucleic acid complementary to the HCV RNA, and
    wherein said contacting comprises
    contacting the HCV RNA with silica nanoparticles conjugated to a nucleic acid complementary to HCV RNA, removing material that is not bound to the silica nanoparticles,
eluting HCV RNA bound to the silica nanoparticles,
contacting the eluted HCV RNA with cationic silver nanoparticles, and
detecting HCV RNA when the cationic silver nanoparticles aggregate, wherein aggregation of cationic silver nanoparticles is determined colorimetrically by color change from yellow which denotes substantially non aggregated nanoparticles to colorless or to white which denotes aggregated nanoparticles.

10. A method for detecting a target molecule comprising:
contacting a sample suspected of containing the target molecule with silica or magnetic nanoparticles that are bound to a capture probe or capture ligand for said target molecule,
separating the silica or magnetic nanoparticles and any target molecule bound to the capture probe or capture ligand from other components of the sample,
separating captured target molecule from the silica or magnetic nanoparticles,
contacting said separated target molecule with positively charged silver nanoparticles that are not bound to capture probes or capture ligands, and
selecting a sample containing the target molecule when the silver nanoparticles aggregate in comparison with a control sample that does not contain the target molecule to be detected;
wherein the target molecule is a protein,
wherein the silica or magnetic particles are bound to a capture ligand for the protein, and
wherein nanoparticle aggregation is determined colorimetrically by a color change from yellow which denotes substantially nonaggregated silver nanoparticles, to colorless or to white which denotes aggregated silver nanoparticles.

\* \* \* \* \*